(12) United States Patent
Wang

(10) Patent No.: US 8,361,294 B2
(45) Date of Patent: *Jan. 29, 2013

(54) MONOLITHIC ELECTROPHORESIS GEL SYSTEM

(76) Inventor: Yi Wang, Southbury, CT (US)

( * ) Notice: Subject to any disclaimer, the term of this patent is extended or adjusted under 35 U.S.C. 154(b) by 92 days.

This patent is subject to a terminal disclaimer.

(21) Appl. No.: 12/792,953

(22) Filed: Jun. 3, 2010

(65) Prior Publication Data

US 2010/0326829 A1 Dec. 30, 2010

Related U.S. Application Data

(63) Continuation-in-part of application No. 12/492,188, filed on Jun. 26, 2009.

(51) Int. Cl.
*G01N 27/453* (2006.01)
*G01N 27/447* (2006.01)

(52) U.S. Cl. ........................................ 204/466; 204/616

(58) Field of Classification Search .......... 204/606–621, 204/456–470
See application file for complete search history.

(56) References Cited

U.S. PATENT DOCUMENTS

| | | | |
|---|---|---|---|
| 3,719,580 A * | 3/1973 | Roberts et al. ................. | 204/619 |
| 5,384,022 A | 1/1995 | Rajasekaran | |
| 6,036,021 A | 3/2000 | Moi | |
| 6,231,741 B1 * | 5/2001 | Tuurenhout et al. .......... | 204/618 |
| 6,749,733 B1 | 6/2004 | Sibbet | |
| 6,942,775 B1 * | 9/2005 | Fox ................................ | 204/467 |
| 2002/0100690 A1 * | 8/2002 | Herbert .......................... | 204/610 |
| 2004/0050699 A1 * | 3/2004 | Goncalves ..................... | 204/450 |
| 2005/0023139 A1 | 2/2005 | Rooney et al. | |
| 2006/0163067 A1 | 7/2006 | Sevigny et al. | |

FOREIGN PATENT DOCUMENTS

| | | |
|---|---|---|
| DE | 102005041638 | 3/2007 |
| EP | 0493996 | 7/1992 |
| EP | 0505929 | 9/1992 |
| WO | 9610743 | 4/1996 |
| WO | 9947255 | 9/1999 |
| WO | 2005047882 | 5/2005 |

* cited by examiner

*Primary Examiner* — J. Christopher Ball
(74) *Attorney, Agent, or Firm* — DeLion & Peterson, LLC

(57) ABSTRACT

Apparatus, systems and methods for performing gel electrophoresis using a monolithic electrophoresis unit that at least includes first and second chambers containing one or more buffer solutions and a gel chamber containing a pre-cast gel, whereby all of these chambers are integrated into a prefabricated single unit that is ready for use. In performing gel electrophoresis, a top seal of this monolithic electrophoresis unit is removed, followed by optionally removing a gel chamber seal from over the gel chamber, such that, buffer solution contacts the pre-cast gel within the gel chamber. Target samples are loaded into the gel chamber for contact with the pre-cast gel, a reusable lid is attached to the top surface of the monolithic electrophoresis unit, and an electrical connection is provided through the reusable lid into the monolithic electrophoresis unit for performing electrophoresis on the pre-cast gel.

20 Claims, 19 Drawing Sheets

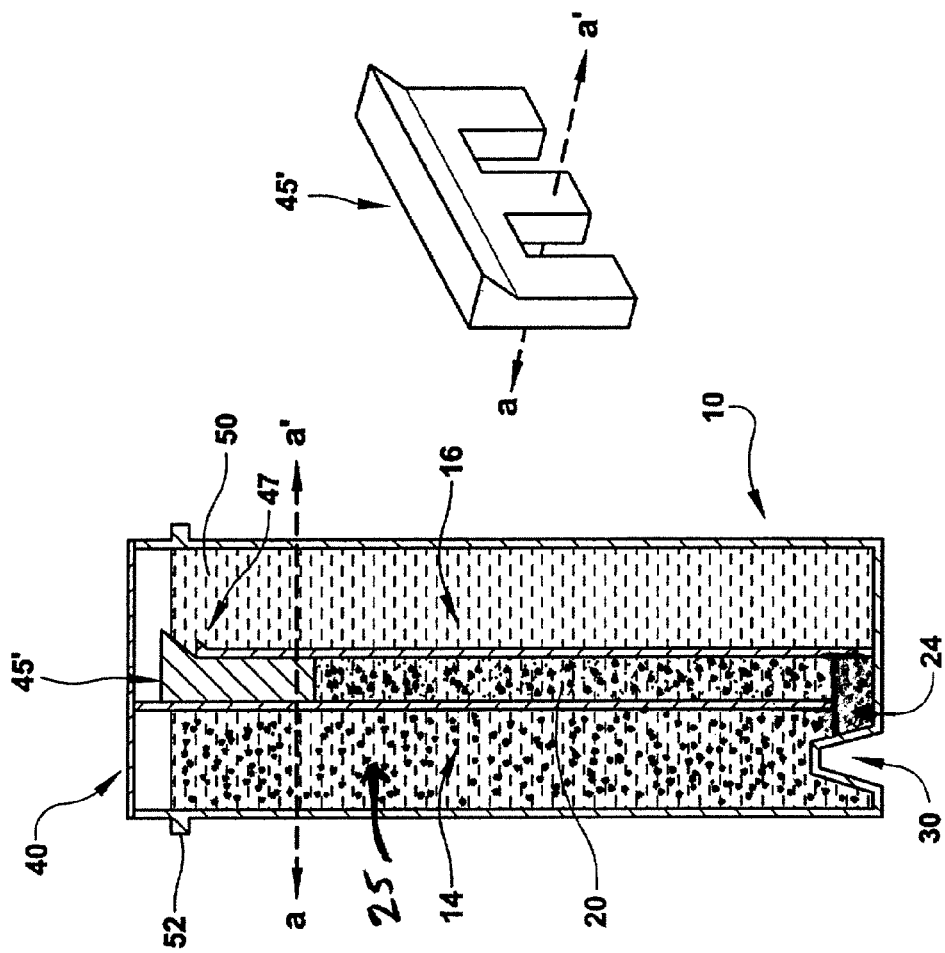
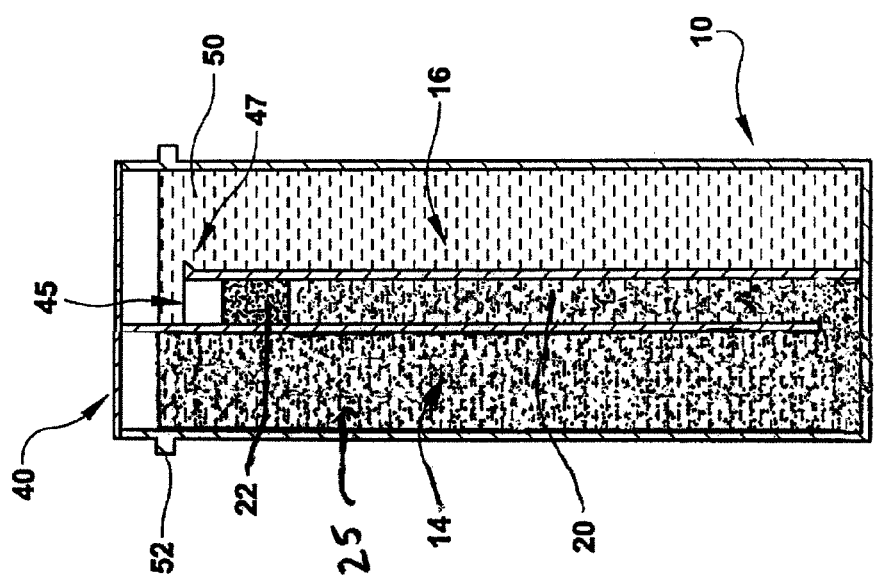

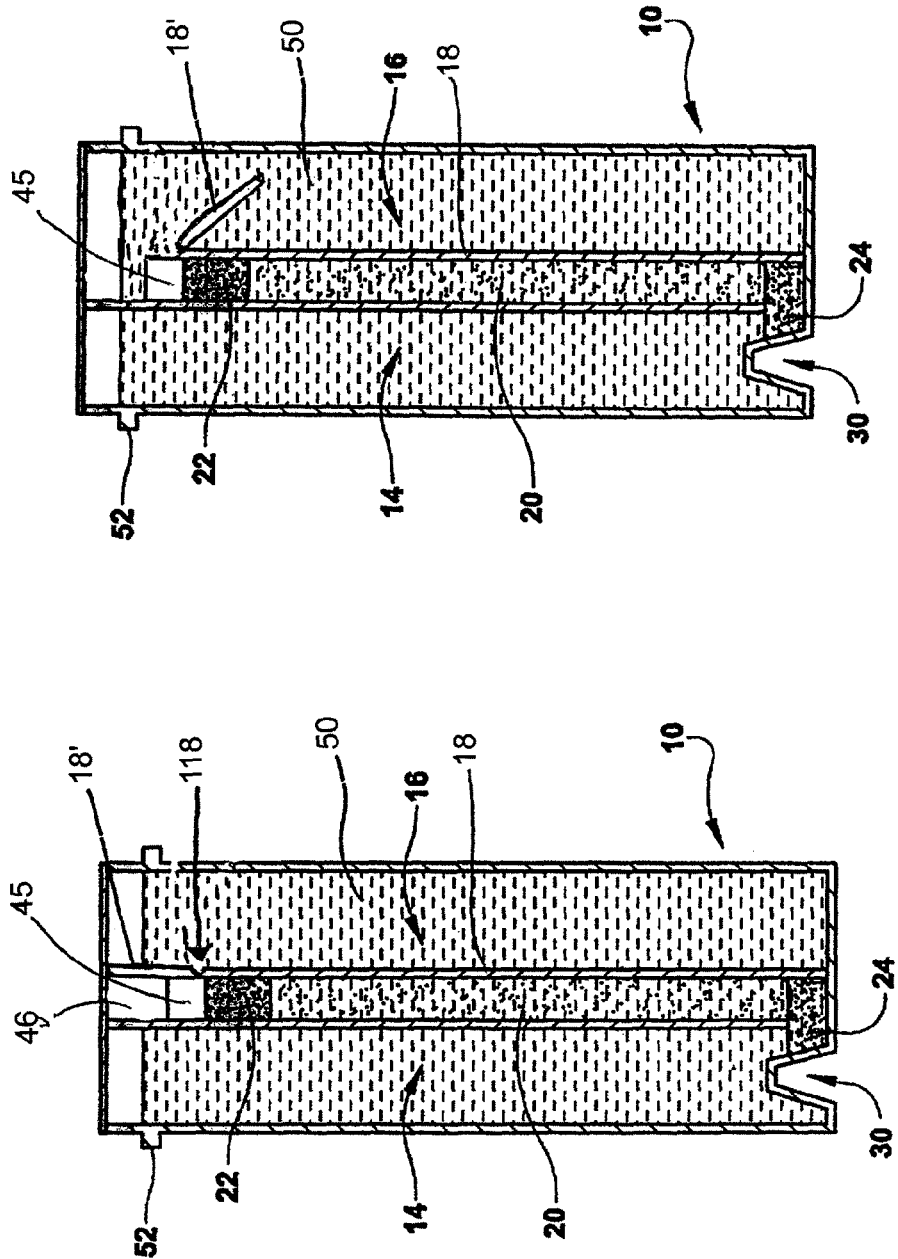

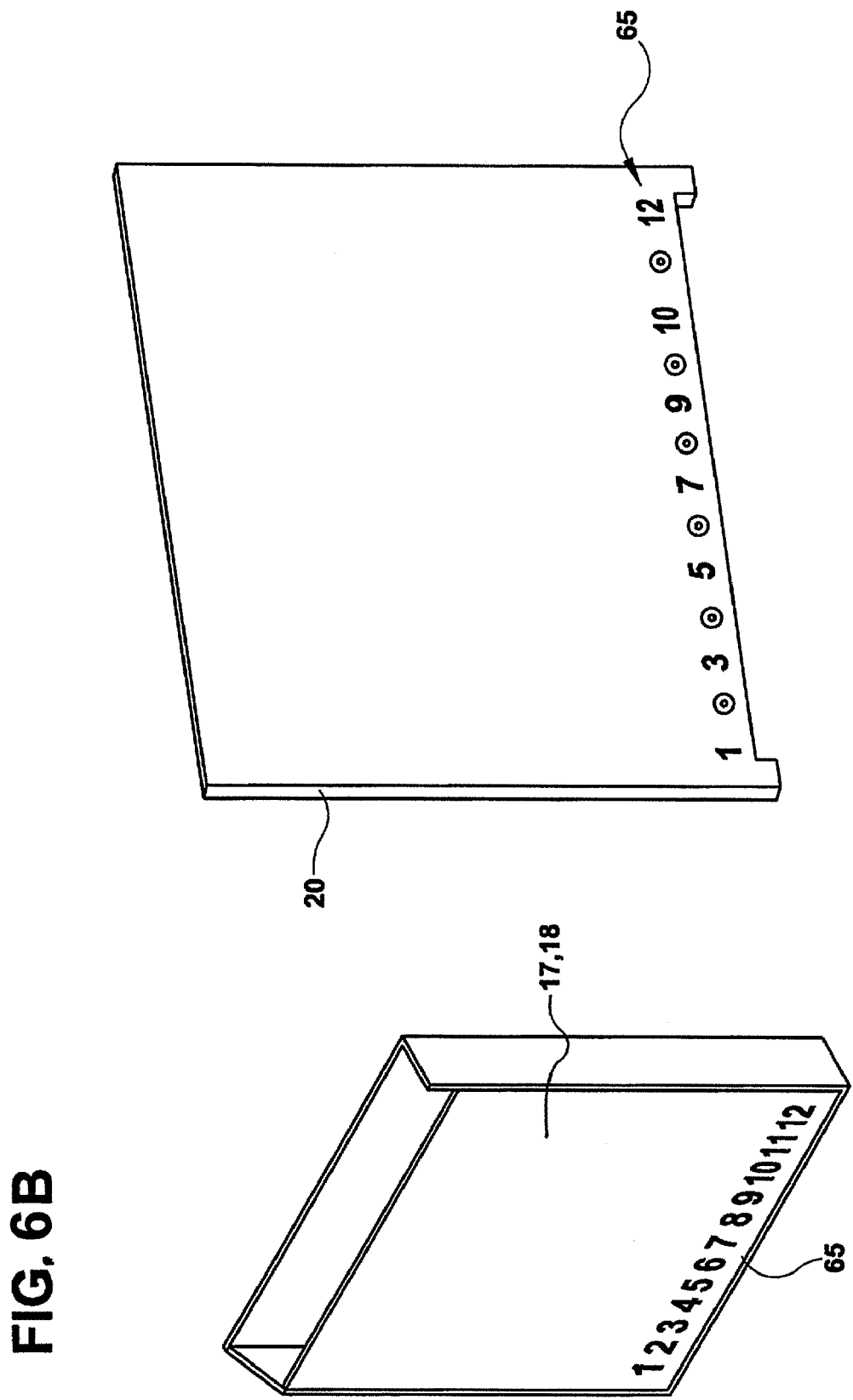

1 2 3 4 5 6 7 8 9 10 11

MONOLITHIC ELECTROPHORESIS GEL SYSTEM

This application is a Continuation-in-Part application of pending application Ser. No. 12/492,188, filed Jun. 26, 2009.

BACKGROUND OF THE INVENTION

1. Field of the Invention

The present invention is directed to gel electrophoresis, and in particular, to a pre-cast vertical monolithic gel electrophoresis system and an electrophoresis method using the present monolithic system.

2. Description of Related Art

Gel electrophoresis is known for separating and purifying protein, peptide DNA, RNA, and a variety of electrically charged macromolecules for the study thereof, or as a preparative step for subsequent analytical procedures. For instance, gel electrophoresis is often used to separate and purify molecules for protein purity verification, protein identification, subsequent DNA sequencing, blotting procedures, mass spectrometry, PCR, RFLP, cloning, or other known techniques for further characterization.

In vertical electrophoresis, a gel matrix is placed in a buffer-filled electrophoresis tank such that the gel is submerged just beneath the buffer surface vertically. The gel matrix is of a material having both a composition and porosity suitable for the specific molecular weight, size and composition of the target molecules to both contain and separate these target molecules. The gel matrix also has wells for receiving alloquots of the target sample to be tested. The electrophoresis tank has cathode and anode terminals on opposite sides of the gel matrix, such that, once the target samples reside in the gel matrix, an electric current is applied to the matrix for generating an electric field. This electric field separates the charged molecules suspended in the gel matrix, whereby negatively charged molecules move in bands through the matrix at different rates toward the anode, while positively charged molecules move in bands through the matrix also at different rates toward the cathode.

In a conventional electrophoresis assembly, the electrophoresis box is composed of two separate flat plates separated by spacers for holding a gel. The electrophoresis apparatus is assembled by providing a gel either vertically or horizontally between these flat plates. This gel may be a pre-cast (i.e., prefabricated) gel that is removed from its packaging and placed between the two flat plates, or it may be mixed by the user assembling the electrophoresis apparatus, poured into a gel mold between the plates and then allowed to set for several hours to form a gel. The electrophoresis tank also includes two reservoirs for containing a buffer solution, whereby each reservoir is on opposite sides of the gel and has an electrode therein. Once the gel is provided between the plates, a buffer solution is poured into each of these reservoirs so that the buffer covers the gel and the electrodes reside within the buffer. With the samples to be tested residing in wells of the gel, an electric current is then applied to the assembly via the electrodes to generate an electric field across the gel for separating the charged molecules in such gel. The gel is then removed for subsequent analytical procedures, and the equipment must be thoroughly washed for reuse.

However, these conventional gel electrophoresis assemblies and approaches are lengthy, and require a significant amount of processing steps and skill in preparing the gel, assembling the apparatus and running the gel. These approaches also require a large amount of buffer to run the gel, typically greater than 750 ml, and are prone to leakage due to the apparatus being improperly assembled. Additionally, these conventional gel electrophoresis systems that include the buffer tank, various clamps and gel holders, buffer dam and tank cover, and supplies for running gels are expensive, bulky and require washing and maintenance thereof after performing an electrophoresis run.

Accordingly, a need continues to exist for improved electrophoresis assemblies that are easy to use, require minimal processing and handling steps, are structurally and mechanically stable, time efficient, and are low cost.

SUMMARY OF THE INVENTION

Bearing in mind the problems and deficiencies of the prior art, it is therefore an object of the present invention to provide a prefabricated, monolithic gel electrophoresis apparatus that is ready to use for electrophoresis.

It is another object of the present invention to provide an electrophoresis method using a prefabricated, monolithic gel electrophoresis apparatus.

A further object of the invention is to provide a prefabricated monolithic gel electrophoresis apparatus that can be used directly without assembly or modification thereto.

Another object of the present invention is to provide a prefabricated, monolithic gel electrophoresis apparatus that is inexpensive and requires minimal handling and preparation for use in electrophoresis.

It is yet another object of the present invention to provide a prefabricated monolithic electrophoresis system that requires no washing, maintaining and storing of a buffer tank and various other components (e.g., clamps, gel holders, etc.)

Still other objects and advantages of the invention will in part be obvious and will in part be apparent from the specification.

The above and other objects, which will be apparent to those skilled in the art, are achieved in the present invention which is directed to one-piece electrophoresis apparatuses for use in performing gel electrophoresis. These one-piece electrophoresis apparatuses at least include first and second buffer chambers containing the same or different buffer solutions with a gel chamber there-between. The gel chamber contains a pre-cast gel that at least includes a separating gel matrix. These gel chamber and first and second buffer solution chambers are integrated with each other into a single unit that comprises a molded monolithic electrophoresis unit that is ready for use.

In another aspect, the invention is directed to systems for use in performing gel electrophoresis. These systems at least include a reusable lid and a pre-fabricated monolithic electrophoresis unit. This unit includes an anode chamber and a cathode chamber both containing the same or different buffer solutions, and a gel chamber. The gel chamber is integrated with and resides between the anode and cathode chambers, and contains a pre-cast gel. This entire pre-fabricated monolithic electrophoresis unit is ready for use in performing gel electrophoresis. The system also includes an electrical connection between the reusable lid and the pre-fabricated monolithic electrophoresis unit for performing the gel electrophoresis.

In still another aspect, the invention is directed to methods for performing gel electrophoresis. These methods at least include providing a monolithic electrophoresis unit that has a unit seal on a top surface thereof. This monolithic electrophoresis unit includes anode and cathode chambers containing the same or different buffer solutions and a gel chamber having a gel chamber seal. The gel chamber is integrated with and resides between the anode and cathode chambers and contains a pre-cast gel. The methods further include removing both the unit seal and the gel chamber seal. A target sample is then loaded into the monolithic electrophoresis unit, followed by attaching a reusable lid to the top surface of such unit. Electrophoresis is then performed on the pre-cast gel by providing an electrical connection through the reusable lid into the monolithic electrophoresis unit.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIGS. 4A-F are cross-sectional views of alternate embodiments of prefabricated, monolithic gel electrophoresis units in accordance with the invention.

FIGS. 5A-B are cross-sectional views of one or more embodiments of the invention showing a movable interior wall within the electrophoresis unit that separates the gel chamber from the cathode chamber prior to use and allows buffer solution into the gel chamber just prior to use of the unit.

FIG. 6A-B are perspective views showing pre-cast well indicators and/or sample wells in the buffer chambers and/or the separating gel matrix in accordance with the invention.

DESCRIPTION OF THE PREFERRED EMBODIMENT(S)

Figure 1A:
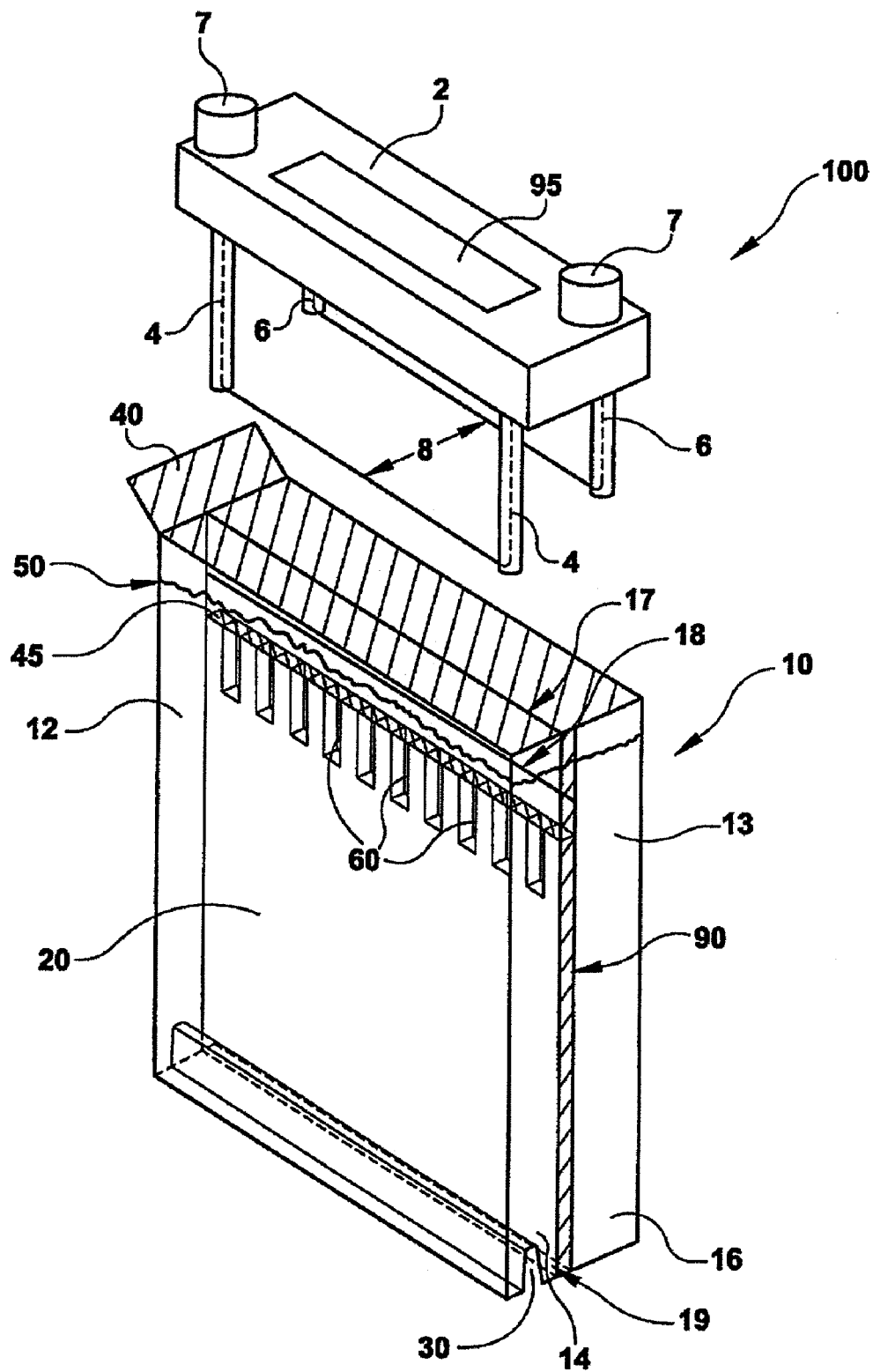
FIG. 1A is a perspective view of a prefabricated, monolithic gel electrophoresis unit and system according to one or more embodiments of the present invention.

In describing the preferred embodiment of the present invention, reference will be made herein to FIGS. 1A-10 of the drawings in which like numerals refer to like features of the invention.

The present invention is directed to apparatus, systems and methods for performing gel electrophoresis using a monolithic (i.e., one-piece), prefabricated gel electrophoresis assembly that includes a gel matrix and buffer, whereby the assembly is ready to use for electrophoresis. The present apparatus and systems are compact, all-in-one units that integrate the gel chamber with two or more electrophoresis running chambers into a single, molded unit that is structurally stable and prevents leakage. In one or more embodiments, the gel chamber resides between at least two electrophoresis running chambers whereby a first chamber contains a buffer solution that is different from the buffer solution used to make the gel (e.g., a buffer cathode chamber) while the second chambers also contains a buffer solution different from the buffer solution contained in the gel (e.g., a buffer anode chamber).

In alternative embodiments, the gel chamber resides between at least two electrophoresis running chambers whereby a first of such chambers (e.g., the cathode chamber) contains a buffer solution different from the buffer solution used to make the gel (e.g., a buffer cathode chamber) while the second of such chambers (e.g., the anode chamber) contains a buffer solution that is the same as the buffer that is used to make the gel matrix (e.g., a gel running buffer solution anode chamber).

An advantage of using the same buffer in both the anode and gel chambers is that the buffer in the anode chamber may directly contact the gel matrix made using the same buffer and residing in the gel chamber. As such, it is not necessary to provide a base sealing gel between the anode and gel chambers to prevent contact between the buffer in the anode chamber and the gel matrix (which is made using a different buffer) residing in the gel chamber. As discussed in detail below, a base sealing gel is preferred when a different buffer resides in the anode chamber as that buffer used to make the gel matrix since during storage and transportation the different anode buffer may degrade or chemically alter the gel matrix. By using the same buffer in both the anode chamber and to make the gel matrix there is no need to prevent the contact between the anode buffer and the gel matrix because they contain the same buffer. Diffusion between the two will not change the chemical properties of either one.

The entire system, as described in detail below, includes only two components, in particular, a reusable lid having electrodes and a disposable pre-fabricated electrophoreses unit having gel chamber(s) integrated with at least two electrophoresis running chambers that may contain a buffer solution and/or a gel running buffer solution. Preferably, the system is a pre-cast vertical monolithic gel electrophoresis system.

Figure 1B:
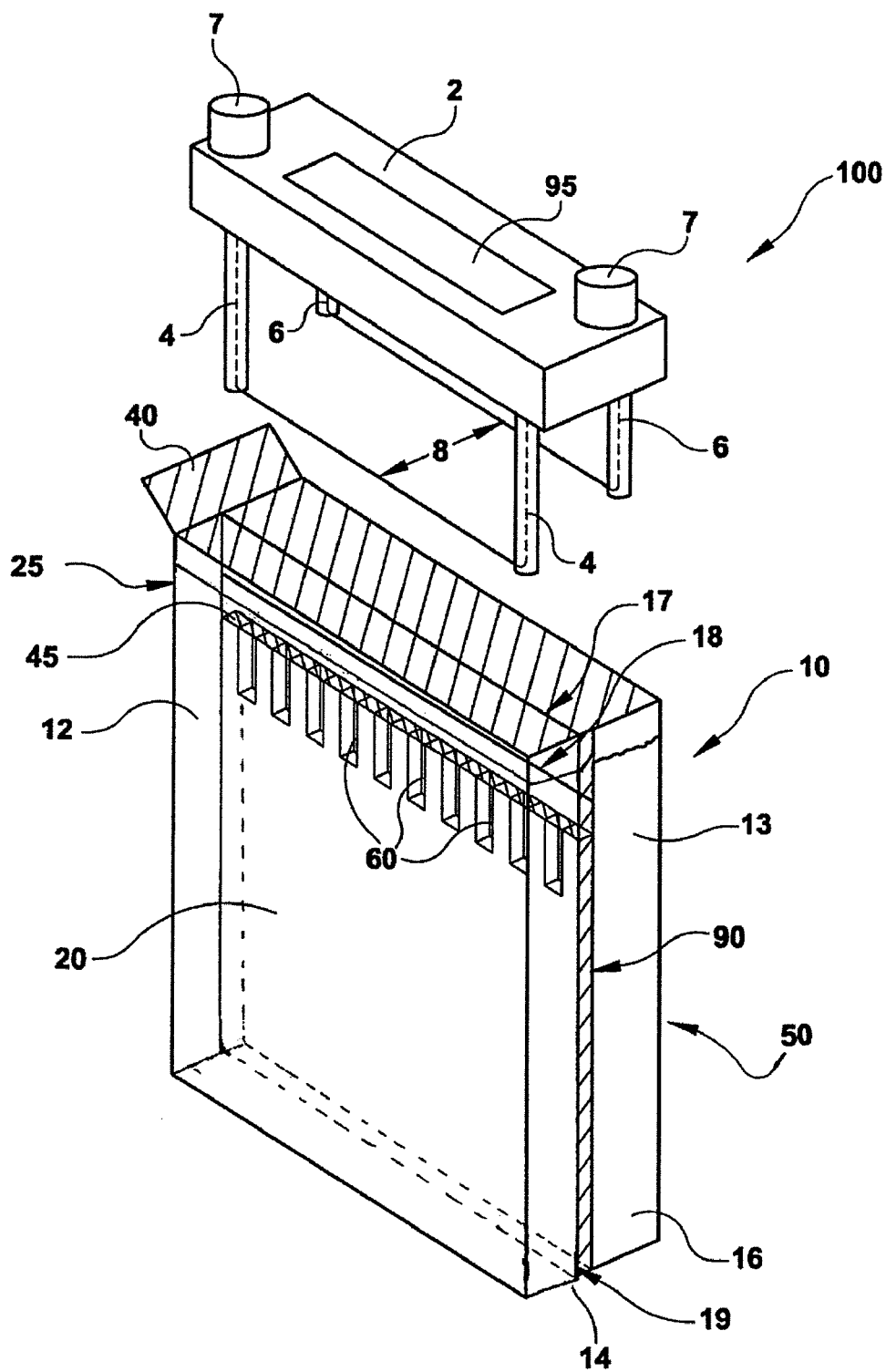
FIG. 1B is a perspective view of a prefabricated, monolithic gel electrophoresis unit and system according to one or more alternate embodiments of the invention

Referring now to FIGS. 1A-B, one embodiment of a gel electrophoresis assembly 100 is shown according to the present invention. The assembly 100 includes a reusable lid 2 having at least two electrodes 4, 6 and a pre-fabricated, monolithic gel electrophoresis unit 10. As shown, the lid 2 includes at least a pair of openings for receiving a first connector 7 that is electrically connected to a power source and a second connector 7 that is also electrically connected to the power source. Optionally, as shown in FIG. 1A, the lid may include a moveable window 95 on a top surface of the lid, whereby this window 95 is movable from an opened to closed position, and vice versa. The window 95 is beneficial in the event additional buffer or target sample needs to be added inside the unit 10 during an electrophoresis run. Alternatively, referring to FIG. 2E, a liquid crystal display 96 may reside at the top surface of the lid 2. This liquid crystal display 96 is preferably thermally connected to one or more of the buffer chambers for measuring and providing the temperature of the running buffer during an electrophoresis run.

FIGS. 2A-E show one or more embodiments of the present reusable lid 2. As is shown, the lid 2 is constructed of a rigid material, such as a rigid plastic, glass or a glass material (e.g., acrylic plastic or glass). The lid 2 may include a seal 3 located at or near the bottom surface thereof for providing a secure and leak-proof fit between the lid 2 and unit 10 once assembled together. Attached to the lid are downwardly extending rods 1 for protecting an electrode wire 8 therein from damage and distortion during use, handling and storage of the lid. The electrode wire 8 is composed of an electrically conductive material including, but not limited to, platinum, titanium, platinized titanium, and the like. The lid 2 includes a pair of anode electrodes 4 for providing a negative electrical charge to a solution residing within a first chamber of the electrophoresis unit 10, and a pair of cathode electrodes 6 for providing a positive electrical charge to a solution residing within a second chamber of unit 10. While the drawings show the pairs of electrodes 4, 6 in electrical communication with one another via conductive wires, it should be appreciated that a single anode and cathode may be used in each electrophoresis running chamber, or even additional connectors 7 may be used to provide the corresponding electrical charge from outside the assembly 100.

Figure 2A:
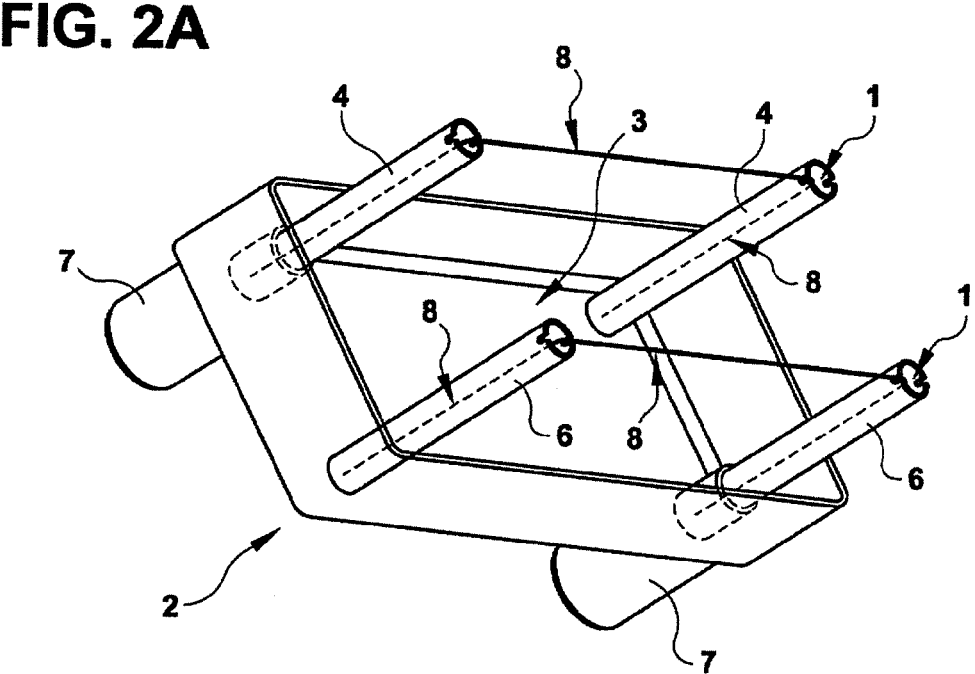
FIGS. 2A-E are perspective views showing one or more embodiments of a reusable lid in accordance with the invention.
Figure 2B:
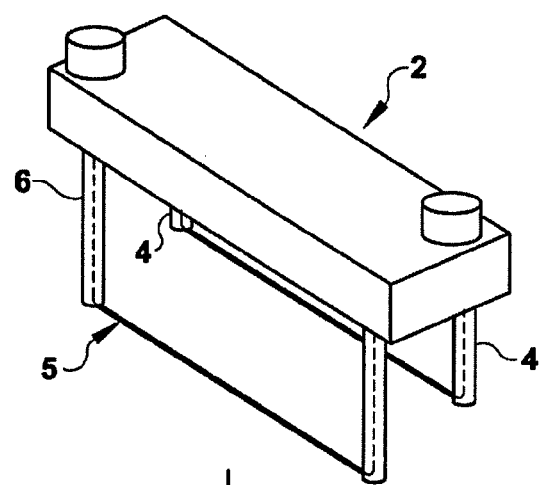
Figure 2C:
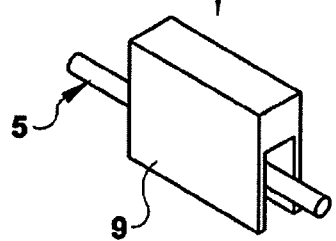
Figure 2D:
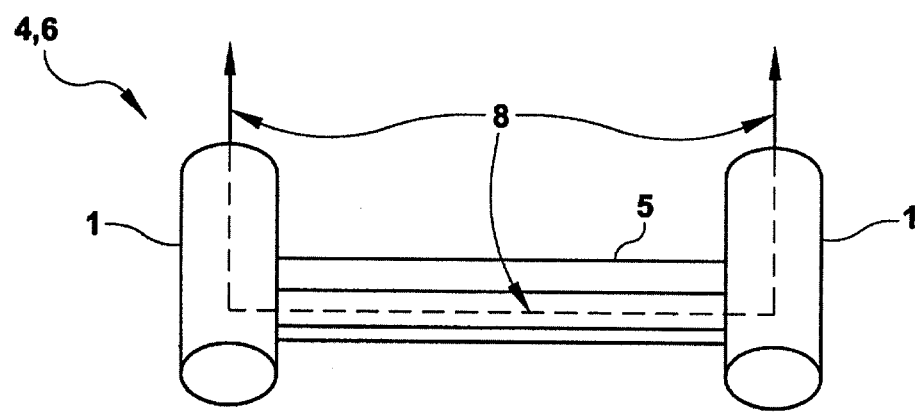
Figure 2E:
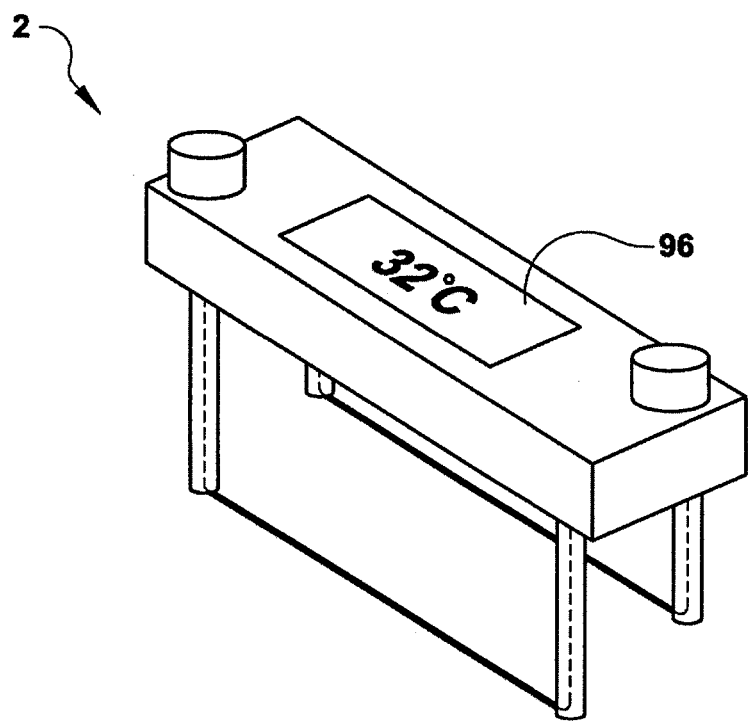

Referring to FIG. 2D, each of the anode and cathode electrodes 4, 6 include the conductive electrode wire 8 that extends down from the respective connector 7 (not shown), through a first protective rod 1 of the lid and across to an adjacent protective rod 1 of the lid. These protective rods 1 may be molded as part of the lid during fabrication thereof. As an alternative, the rods may be securely attached to the lid as separate components, such that, the electrodes 4, 6 and/or connectors 7 are removable and replaceable. The protective rods 1 preferably each have a notch at an end thereof for receiving and holding the electrode wire 8 in position.

The lid may also include a protective bar 5 of a rigid material that encases the wire 8 as it extends from one rod to an adjacent rod for the protection of such wire 8. This protective bar 5 may also be molded as part of the lid, or alternatively, it may be securely attached to the lid as a separate component whereby this protective bar 5 is received, held and secured by the notches at the ends of the rods 1. Referring to FIG. 2C, the lid may further include a notched guard 9 for receiving and protecting the protective bar 5 (if present) and/ or the electrode wire 8 from damage, distortion and/or breakage. That is, the notch of guard 9 protects either the wire 8 itself, or if the wire 8 is encased by the protective bar 5, then the guard 9 protects both the bar 5 and the encased wire 8. Like rods 1 and bar 5, this notched guard 9 may also be molded as part of the lid or it may be a separate component that is securely attached to the lid. The notched guard 9 is attached to an inside surface of the lid and may either extend partially between the electrodes 4, 6; or it may extend entirely between the electrodes and have a first downwardly extending sidewall attached between and directly to the pair of anode electrodes 4 and a second downwardly extending sidewall attached between and directly to the pair of cathode electrodes 6.

The lid 2 is preferably fabricated with an attachment control(s) that allows the lid to be attached to the pre-fabricated, monolithic gel electrophoresis unit 10 in one direction only so that the positive anode electrodes 4 are aligned with an anode chamber 14 while the negative cathode electrodes 6 are aligned with a cathode chamber 16 of unit 10. In doing so, both the lid 2 and the unit 10 may each include attachment controls of an alignment indicator (e.g., color coding, symbols, numbers, letters, etc.) to ensure that the lid 2 is correctly attached to unit 10. Alternatively, the lid 2, unit 10, or lid 2 and unit 10 together, may be fabricated with attachment controls of mating patterns or design(s) (e.g., notches, lips, edges, rims, grooves, male-female matings, etc.) that prohibit the lid 2 from being incorrectly attached to the unit 10.

In accordance with embodiments of the invention, the pre-fabricated, monolithic gel electrophoresis unit 10 is a molded one-piece electrophoresis box of a rigid plastic, glass or a glass material that includes an open top surface and a bottom surface 11 connected to opposing outer walls 12 and opposing sidewalls 13. It should be appreciated that the outer walls, sidewalls and bottom surface each have a thickness that provides the box with sufficient rigidity to withstand handling, transport, and processing procedures. For instance, wherein the box is composed of a rigid plastic material, the thickness of the outer walls, sidewalls and bottom surface may have a thickness of about 1 mm or greater.

Figure 1C:
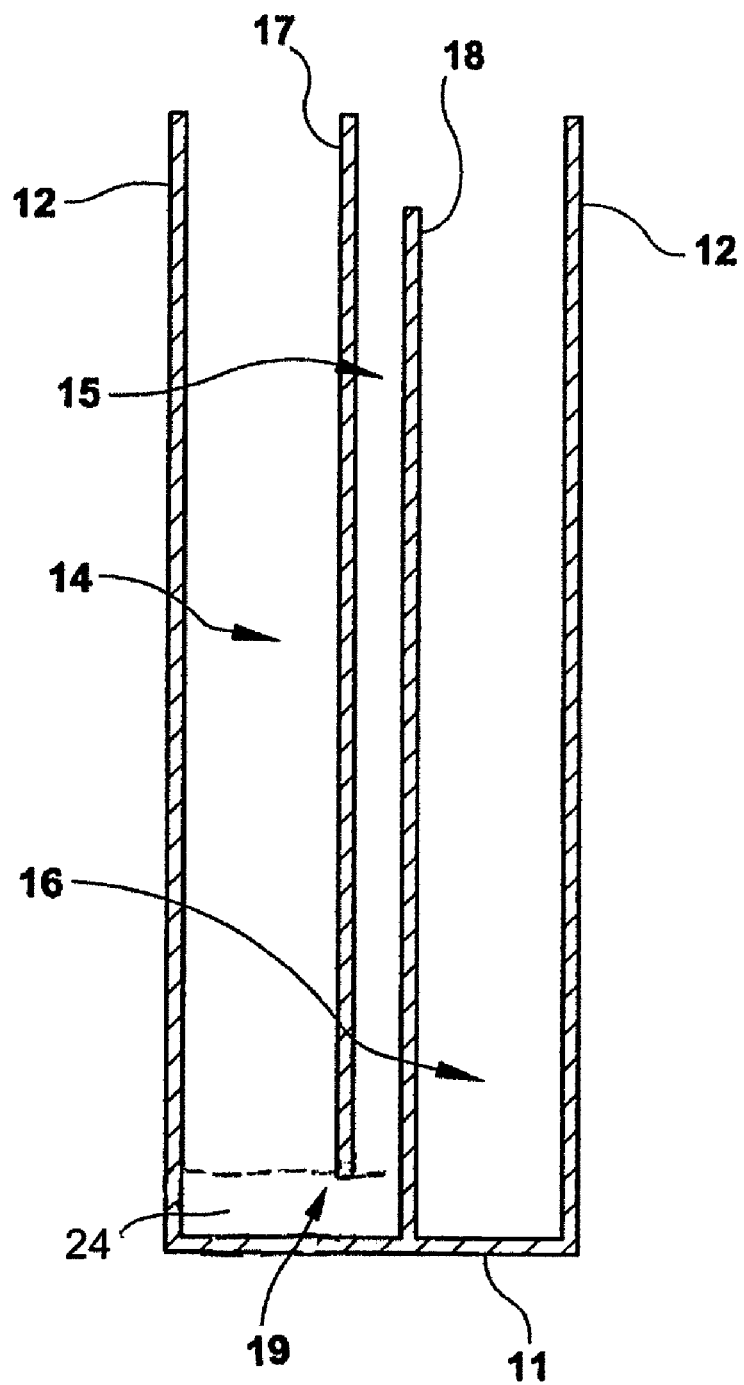
FIG. 1C is a cross-sectional view of the pre-fabricated, monolithic gel electrophoresis unit shown in FIG. 1A and/or FIG. 1B.

As shown in FIG. 1C, the interior of the electrophoresis box includes at least two opposed upstanding interior walls 17 and 18 that are parallel with and spaced apart from the opposing outer walls 12 to form at least three interior chambers within the pre-cast or molded electrophoresis box. These interior chambers include an anode chamber 14, a cathode chamber 16 and a gel chamber 15 between the anode and cathode chambers 14, 16.

The first interior wall 17 is attached to the opposing sidewalls 13 and extends to the open top of the one-piece electrophoresis box to both separate the gel chamber 15 from the anode chamber 14, and to electrically isolate the anode chamber 14 from the cathode chamber 16. The first interior wall 17 also has an opening 19 at the bottom end thereof, which resides at the bottom surface 11 of the box. This opening 19 allows electrical communication between the anode chamber 14 and the gel chamber 15. The second interior wall 18 is also attached to the opposing sidewalls 13 and separates the gel chamber 15 from the cathode chamber 16. This second interior wall 18 has a bottom end in contact with the bottom surface 11 of the box and a top end that resides below the open top of the one-piece electrophoresis box, such that, an electrophoresis running solution (e.g., buffer solution 50) is allowed to contact both the top surface of the gel chamber 15 and the cathode chamber 16 for allowing electrical communication between chambers 15, 16.

The present pre-fabricated, monolithic gel electrophoresis unit 10 also includes a separating gel matrix 20 inside the gel chamber 15, a buffer solution 50 within the cathode chamber 16, and in one or more embodiments either buffer solution within the anode chamber 14 (FIG. 1A, which may be the same as or different from the buffer solution 50 in the cathode chamber) or a gel running buffer solution 25 within the anode chamber 14, which again is the same as the buffer used to make the gel matrix (FIG. 1B). The buffer solution 50 also resides partially within gel chamber 15 during operation, at least over a top surface of the separating gel matrix 20, to both cover the matrix 20 and enable the electrical connection between the cathode chamber 16 and the gel chamber 15. In those embodiments of the invention having a gel running buffer solution 25, the separating gel matrix 20 and this gel running buffer solution 25 may include, but are not limited to, a polyacrylamide gel with a concentration between 2% to 30%, in a Tris[tris(hydroxymethyl)aminomethane)]-Citrate buffer pH 6.8, whereby the concentrations of tris and citrate are about 200 mM. In these embodiments the running buffer may be Tris and Hepes ((4-(2-hydroxyethyl)-1-piperazineethanesulfonic acid) pH 7.8, with a concentration of about 100 mM.

Referring to FIGS. 3A-B and 4A-B, side views of the present pre-fabricated, monolithic gel electrophoresis unit 10 are shown in accordance with one or more embodiments of the invention. At least the gel matrix 20 may be composed of a material having a composition and porosity chosen based on the specific weight and composition of the target to be analyzed and subjected to electrophoresis. That is, the material of the separating gel matrix 20 may have varying compositions, concentrations of constituent chemicals, porosities, strengths, optical transparency, and the like, all of which depend on the target sample. For instance, the separating gel matrix 20 may include, but is not limited to, polyacrylamide gels, argrose gels, or any other gel suitable for use in gel electrophoresis. Likewise, the buffer solution 50 provided in the present pre-fabricated, monolithic gel electrophoresis unit 10, whether it is provided in the cathode chamber 16 alone (FIGS. 4A-B) or both the cathode 16 and anode 14 chambers (FIGS. 3A-B), may also vary depending upon the sample being analyzed and subjected to electrophoresis, as well as depending upon the composition and characteristics of the gel matrix 20 or gel matrices residing within the unit 10. In those embodiments having the gel running buffer solution 25 (FIGS. 4A-B), the gel running buffer solution may have the same composition as the buffer of the gel matrix 20 or it may be insignificantly different therefrom so as to avoid impacting or affecting the chemical characteristics and/or properties of the gel buffer (i.e., the buffer used to make the gel).

Regardless of the compositions of the gel matrix 20, the gel running buffer solution 25 and/or the buffer solution 50, a feature of one or more embodiments of the invention is that each of the gel matrix 20, the gel running buffer solution 25 and/or the buffer 50 may be pre-cast and preloaded into the present monolithic gel electrophoresis unit 10. In this manner, there is no need to prepare and cast a gel matrix prior to performing an electrophoresis run, and no need to make and pour a buffer solution into an electrophoresis tank or chamber, thereby preventing spillage of buffer solution.

Figure 3A:
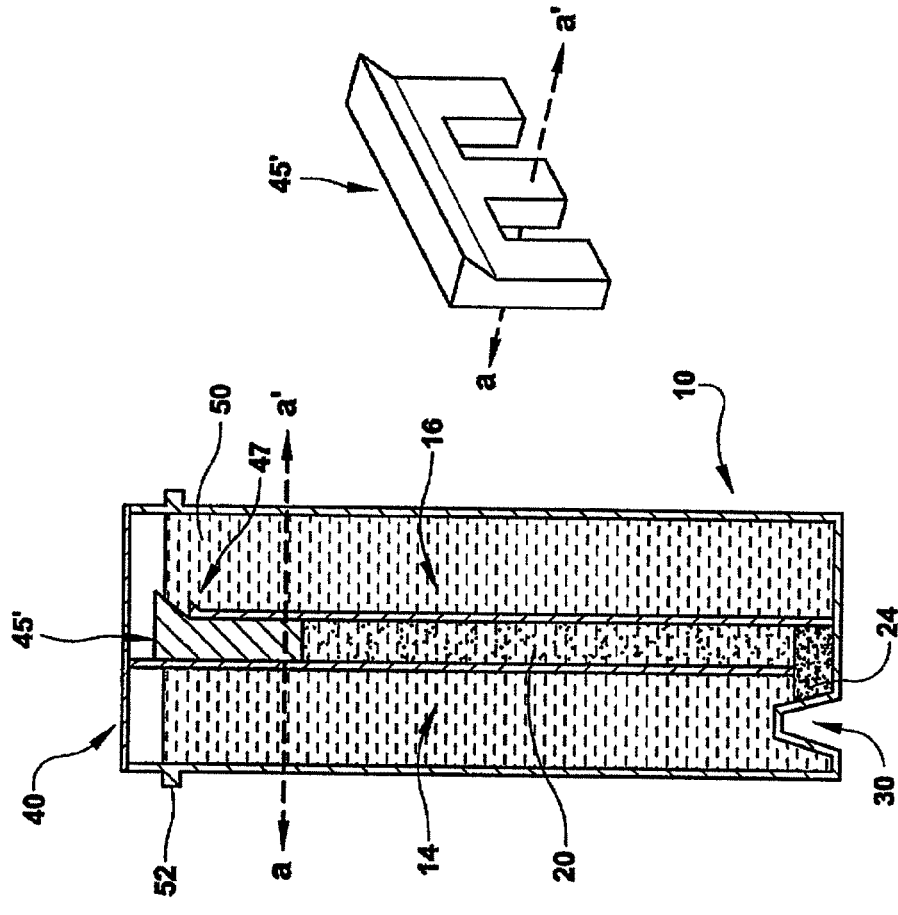
FIGS. 3A-F are cross-sectional views of one or more embodiments of prefabricated, monolithic gel electrophoresis units in accordance with the invention.

FIGS. 3A and 4A show pre-fabricated, monolithic gel electrophoresis units 10 of the invention prior to an electrophoresis run. Referring to FIG. 3A, unit 10 includes buffer solution 50 in both the anode 14 and cathode 16 buffer chambers along with a separating gel matrix 20 in the gel chamber 15, whereby this unit 10 is ready for use and does not require any assembling or fabricating of a gel or buffer prior to performing an electrophoresis run. As alternative embodiments, FIG. 4A shows that the units 10 may include the buffer solution 50 in the cathode chamber 16, a separating gel matrix 20 in the gel chamber 15 and the gel running buffer solution 25 in the anode chamber 14. Again unit 10 of FIG. 4A is ready for use and does not require any assembling or fabricating of a gel or buffer prior to performing an electrophoresis run.

In one or more embodiments, the buffer solution 50 is pre-filled in either both the anode and cathode buffer chambers, or the cathode chamber alone, to a volume marker 52 that resides around a perimeter of the electrophoresis box or at least on the side of the cathode chamber 16. This volume marker 52 may reside on the outside or inside surface of the outer walls 12 (e.g., a color indicating fill line), or it may be etched directly into at least one or both of the outer walls 12. As an alternative to having the buffer pre-loaded to the marker 52, the buffer may be a concentrated buffer solution or powder that is reconstituted to normal strength by adding a liquid, preferably water, to the volume marker 52 prior to performing electrophoresis.

In the present monolithic gel electrophoresis units 10, the separating gel matrix 20 resides entirely inside the gel chamber 15 for separating target molecules. Optionally, a stacking gel 22 may reside over the separating gel matrix 20. The stacking gel 22 is preferably of a different concentration, or even a different composition, than the separating gel matrix 20, and is used to form a number of sample wells over the separating gel matrix 20, which are discussed further below. A base sealing gel 24 may (for example, see FIGS. 3A, 3B, 4B, etc.) or may not reside (for example, see FIG. 4A) at the bottom of the separating gel matrix 20. This base sealing gel 24 is also of a different concentration, or even a different composition, than the separating gel matrix 20. In accordance with one or more embodiments of the invention, the stacking gel 22 and base sealing gel 24 both may be of a different concentration, or a different composition, than the separating gel matrix 20 for allowing easy and effective removal of the separating gel matrix 20 from the unit 10 while avoiding damage to such matrix 20.

In embodiments including the base sealing gel 24 (see, for instance, FIGS. 3A-F, 4B, 4C and 4E), this sealing gel is used to seal the opening(s) 19 between the gel chamber(s) and the anode chamber(s) 14 which, again, may contain either buffer solution 50 or a gel running buffer solution 25. In so doing, the base sealing gel 24 resides in both the gel chamber 15 and the anode chamber 14, such that, it fills opening 19 at the bottom of the first interior wall 17. The sealing gel 24 prevents the separating gel matrix 20 (or matrices) from entering the anode chamber(s) 14 during polymerization, and prevents contact of the separating gel matrix (matrices) with buffer solution 50 or gel running buffer solution 25 residing within the anode chamber 14 during transportation and storage of the unit 10 itself. As such, the base sealing gel 24 is poured into unit 10 prior to the separating gel matrix 20 so that the separating gel 20 does not flow to the anode chamber 14 before it is polymerized.

As shown in FIGS. 1A, 3A-C and 4B an internal beveled notch 30 may reside at the bottom surface 11 of the unit, and extends along the length of the bottom 11 in the anode chamber 14. In those embodiments including the base sealing gel 24, this internal beveled notch 30 aids in retaining the base sealing gel 24 inside the gel chamber 15 and reduces the amount of base sealing gel 24 needed to seal and isolate the separating gel matrix 20 residing in the gel chamber 15 from the buffer solution 50 or gel running buffer solution 25 residing in the anode chamber 14. Alternatively, as shown in FIGS. 1B-C, 3D-F, 4A and 4C-F, the bottom surface 11 of the anode chamber 14 may be planar (i.e., does not have an internal beveled notch 30). In these embodiments as shown in the drawings, the base sealing gel 24 may reside across the entire bottoms of both the anode chamber 14 and the gel chamber 15, or alternatively, it may not be used at all as discussed further below.

Figure 4C:
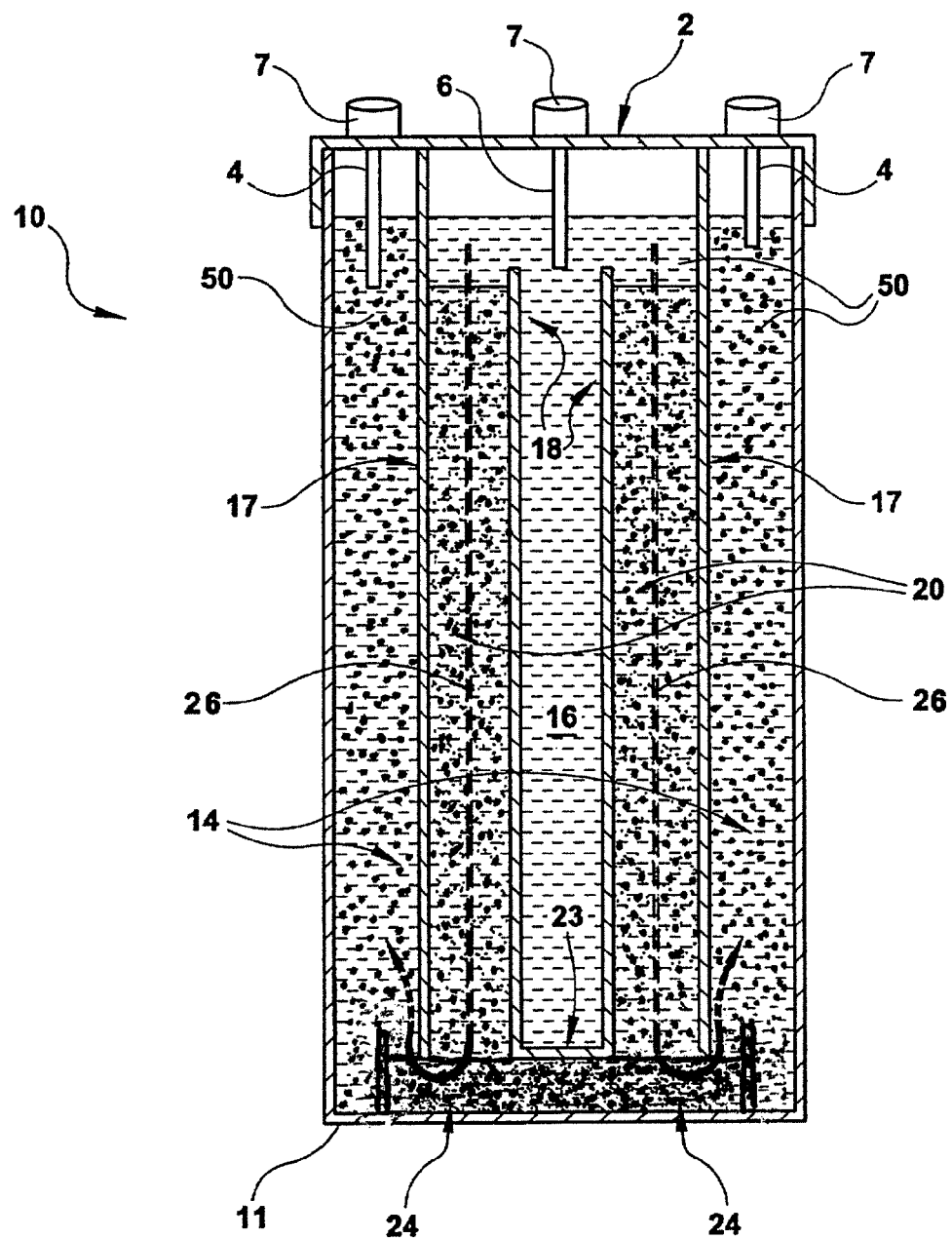
Figure 4D:
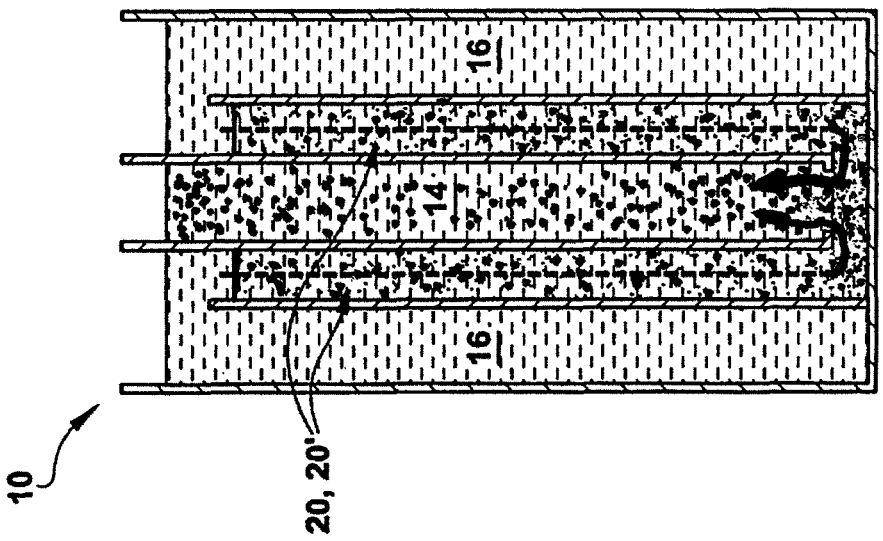
Figure 4E:
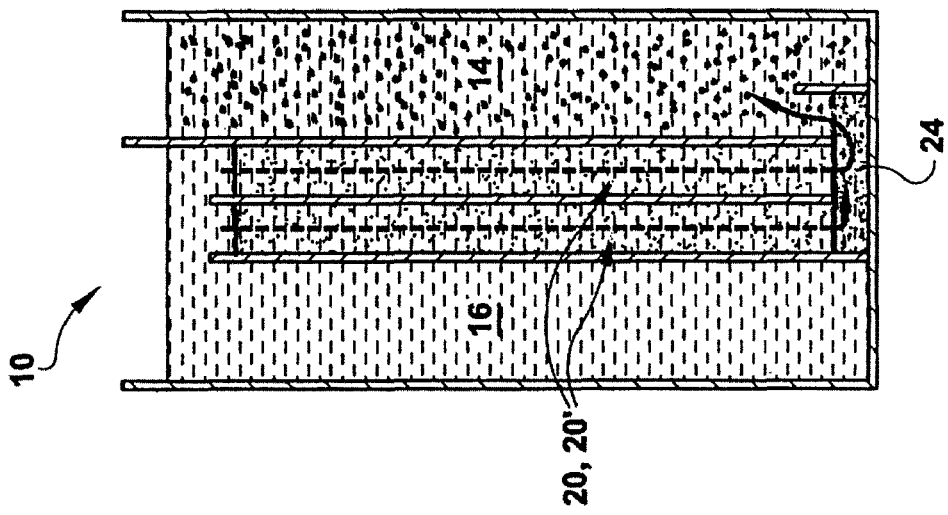
Figure 4F:
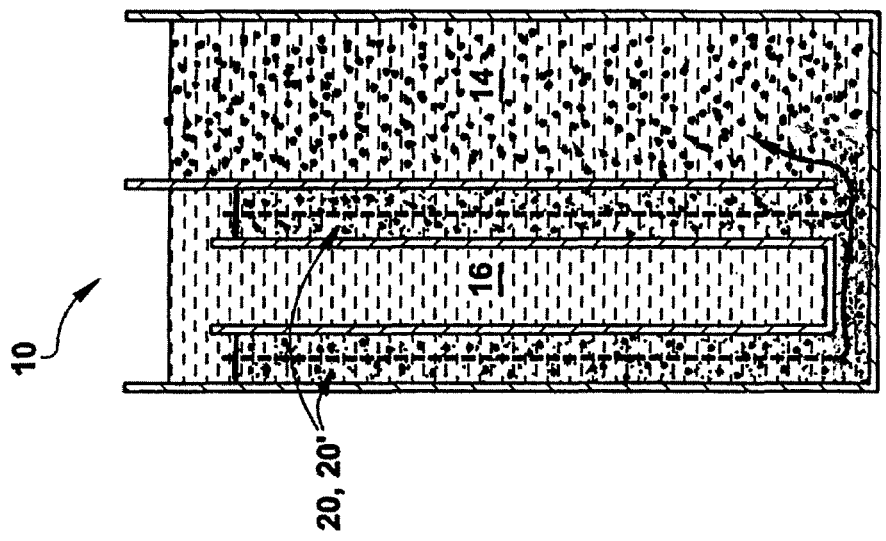

In one or more embodiments, it may not be necessary to have a base sealing gel 24 between the gel chamber 15 and the anode chamber 14 (see, for instance, FIGS. 4A, 4D and 4F). In these embodiments, the compositions of the buffer used to make the separating gel matrix 20 and the gel running buffer solution 25 may be identical or insignificantly different. In embodiments where the gel buffer and the running gel running buffer solution are identical, the gel running buffer solution fills the anode chamber 14 at least to the volume marker 52. The configuration shown in FIG. 1B may be suitable for those embodiments not including the base sealing gel 24 (i.e., where the gel buffer and the running gel running buffer solution are the same in both the gel chamber and the anode chamber).

It should be appreciated that the present prefabricated monolithic gel electrophoresis units 10 are not limited to having a single gel chamber 15 with a single separating gel matrix 20 therein. One or more embodiments of the invention are directed to prefabricated monolithic gel electrophoresis units 10 having various designs that include a plurality of gel chambers 15 each having a separating gel matrix 20 therein. That is, while not departing from the scope of the invention, the prefabricated units 10 may have a single pre-cast gel matrix 20 therein for running a single gel matrix, or alternatively, the prefabricated units 10 may have two or more pre-cast gel matrices 20 residing therein for simultaneously running a plurality of gel matrices.

FIGS. 3C-F and 4C-F show one or more embodiments of multi-gel chambers 15 and/or multi-separating gel matrix (matrices) 20 prefabricated into the monolithic gel electrophoresis units 10 of the invention. Again, multiple gels 20 may be run simultaneously within a single unit 10. Referring to the embodiment of FIGS. 3C and 4C, a first separating gel matrix 20 resides in a first gel chamber, while a second separating gel matrix 20 resides in a second gel chamber. These first and second separating gels in each of the gel chambers both reside within the cathode buffer chamber 16, with a pair of anode chambers 14, 14 on external sides thereof. These pair of anode chambers 14, 14 may either both contain buffer solution 50, both contain gel running buffer solution 25, or one contain buffer solution 50 and the other contain gel running buffer solution 25.

In this aspect, all three chambers 14, 16, 14 are filled with buffer solution 50 and/or gel running buffer solution 25, and are separated from one another by a pair of interior walls 17, with the gel chambers 15 being separated from one another within the cathode buffer chamber by a pair of interior walls 18. A bottom or interior wall 23 resides at the bottom of this buffer chamber 16 to separate the buffer therein from the base sealing gel 24. It should be appreciated that the number of interior walls 17, 18 inside units 10 correspond to the number of buffer chambers 16 and the number of gel chambers 15 within the cathode buffer chamber 16.

As discussed above, each anode chamber 14, 14 may optionally include an internal beveled notch 30 at the bottom surface 11 of the unit 10 for both retaining base sealing gel 24 that resides under each of the separating gel matrices 20 and reducing the amount of such base sealing gel 24 required to fill this region of the unit 10. Again, the base sealing gel 24 prevents entering of separating gel 20 into chamber 14 and prevents contact between the separating gel matrix 20 and the buffer solution 50 or gel running buffer solution 25 residing within the anode chamber 14. The base sealing gel 24 is composed of a material or has a composition that allows it to be easily removed from the separating gel matrix 20, or allows the separating gel matrix 20 to be easily removed from the gel 24. In this manner, after completion of the electrophoresis run, the gel matrix 20 can be easily separated from the unit 10 for further analytical processing.

As discussed above, during the electrophoresis run, a portion of the base sealing gel 24 is in physical contact with the buffer solution 50 or gel running buffer solution 25 in each of the anode chambers 14, 14 to allow electrical communication between each separating gel matrix 20. Since these two separating gel matrices 20 are connected through openings 19 to the two anode chambers 14, such separating gel matrices 20 have the same voltage. This is beneficial in ensuring that the target samples within each of the gel matrices 20 are run at the same rate.

Figure 3B:
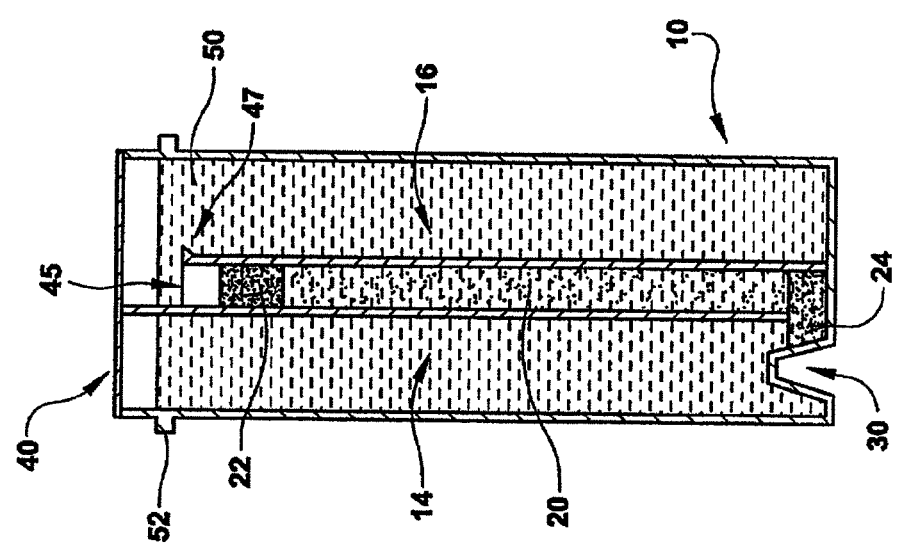
Figure 3C:
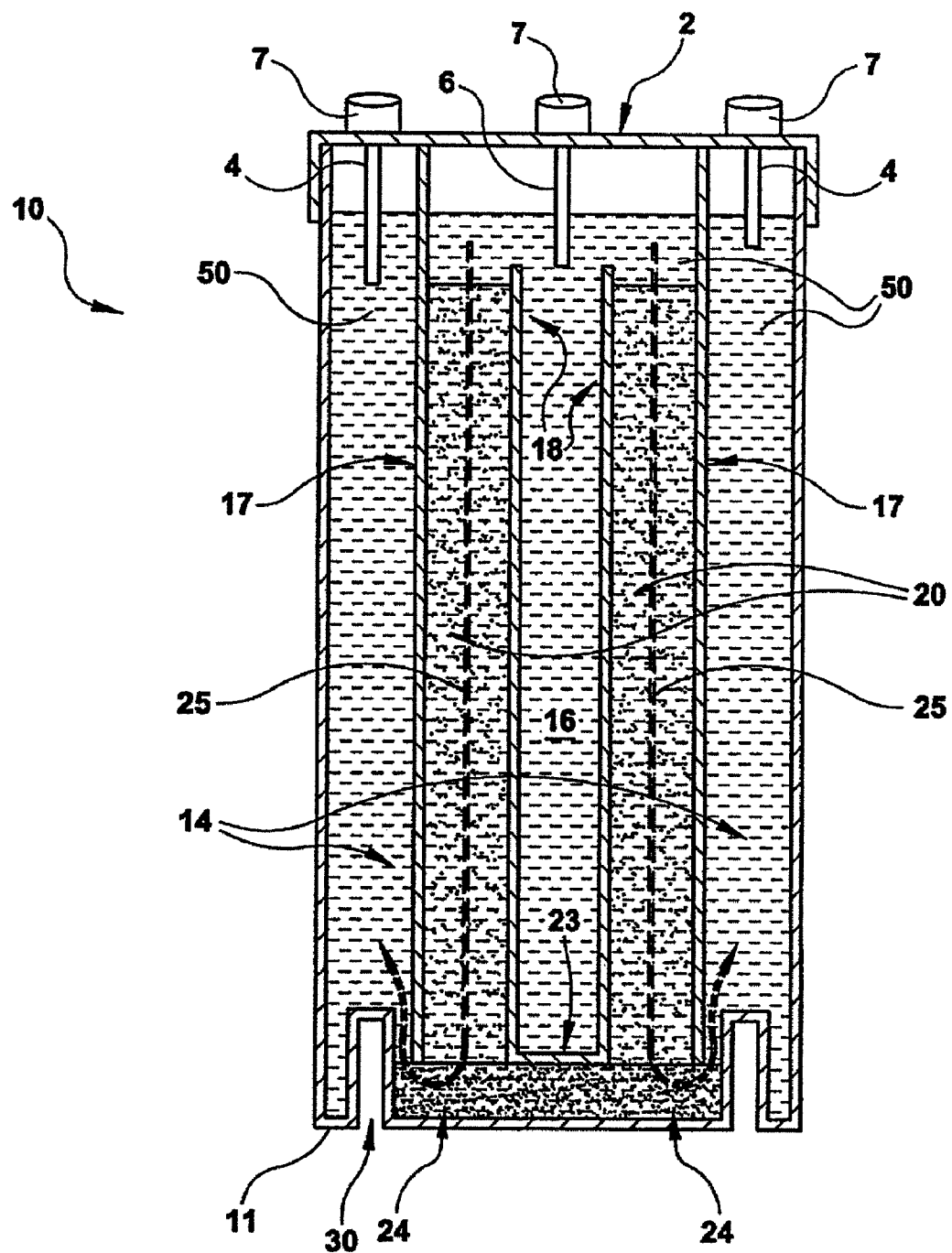
Figure 3D:
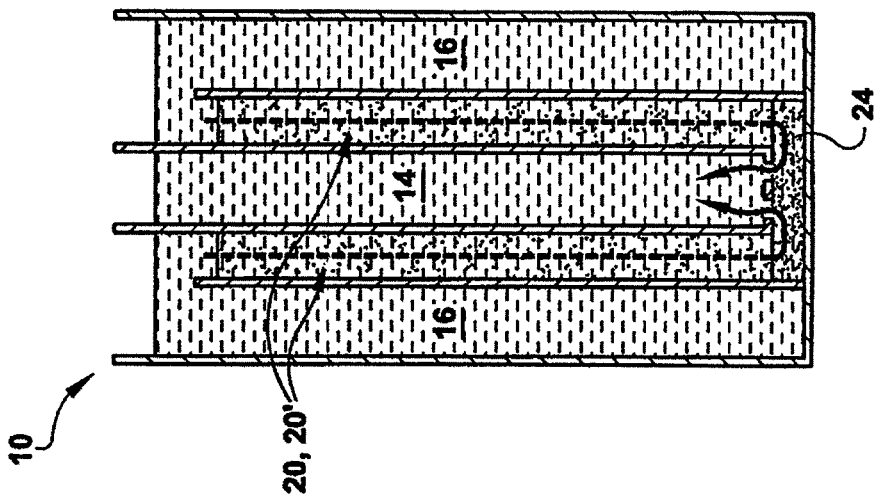
Figure 3E:
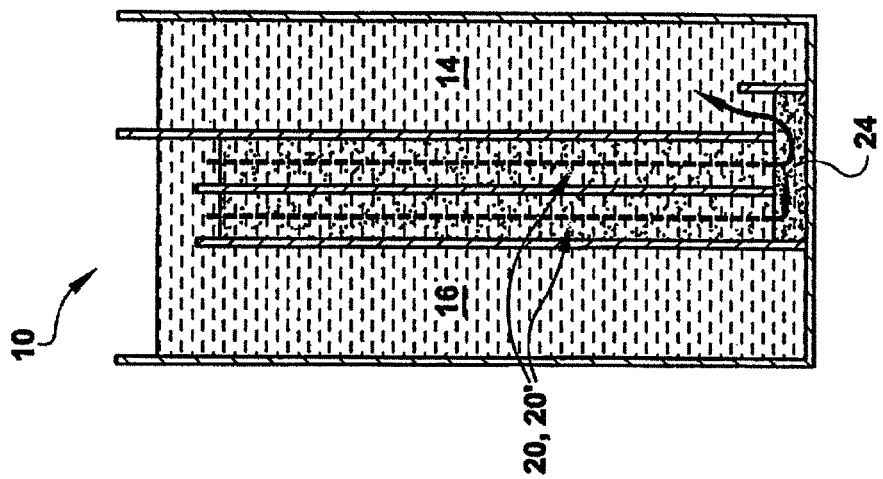
Figure 3F:
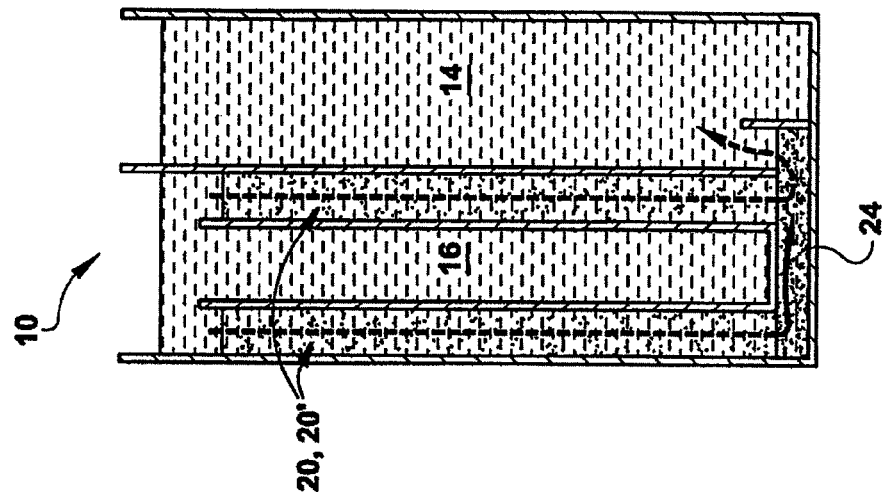

Referring to FIGS. 3D-F and 4D-F, it should be appreciated that there are various embodiments of a multi-gel chamber design that may be employed and prefabricated into the present units 10. For instance, referring to FIGS. 3D and 4D, two or more separating gel matrices 20, 20' may each reside in separate cathode buffer chambers 16, 16', which in turn are separated from one another by an anode chamber 14 filled with either buffer solution 50 or gel running buffer solution 25. The current flows from the cathode buffer chambers 16, 16', through the gel matrices 20, 20' and into the anode chamber 14. Referring to FIGS. 3E and 4E, a single cathode buffer chamber 16 may have two or more separating gel matrices 20, 20' therein that are adjacent one another and separated by an interior wall of the unit, whereby the current flows simultaneously through these two gel matrices, through the base sealing gel 24 and into the anode chamber 14 that contains either buffer solution 50 or gel running buffer solution 25. As another alternative embodiment, as shown in FIGS. 3F and 4F, the unit 10 may have two or more separating gel matrices 20, 20' in a single cathode buffer chamber 16, whereby these gel matrices are separated by interior walls and have buffer solution residing therebetween. The current flows simultaneously through these two gel matrices, through the base sealing gel 24 (if it is present) and into the anode chamber 14. It should be appreciated that many designs and configurations of electrophoresis units 10 having two or more separating gel matrices 20 therein may be implemented in accordance with the various embodiments of the invention.

Referring again to FIGS. 3A-B and 4A-B, prior to performing an electrophoresis run, a seal 45 resides at the top of the gel chamber 15 to isolate and prevent contact between the separating gel matrix 20 (and optionally the stacking gel 22 if present) and the buffer solution 50 residing in the cathode buffer chamber 16. As shown in FIG. 3A, this seal 45 may be a removable tape seal that resides along the entire length of the top of the gel chamber 15. A bevel 47 may reside at the top of the gel chamber 15 to allow and enhance adhesion of the tape seal to the top of the gel chamber.

Alternatively, as is shown in the cross section view of FIGS. 3B and 4B along line a-a', the seal 45 may be a removable gel comb 45' having a beveled top surface for easy and efficient removal thereof. A sealing ring made from rubber can be placed on the top of 18 to further prevent leaking. The gel comb 45' has a plurality of teeth that extend from the beveled top surface into the gel matrix 20 to form a plurality of wells 60 in the gel matrix. It should be appreciated that the gel comb 45' may be provided with any number of downwardly extending teeth to fabricate a corresponding number of wells desired in the resultant unit 10. Since the gel 20 is pre-cast into the unit 10 along with the corresponding number of wells, the need to make a gel and fabricate wells therein is avoided. Once an electrophoresis run is to be performed, the seal 45 is removed to reveal the plurality of wells 60 extending into the gel matrix 20, which are to be used for sample loading.

Figure 7:
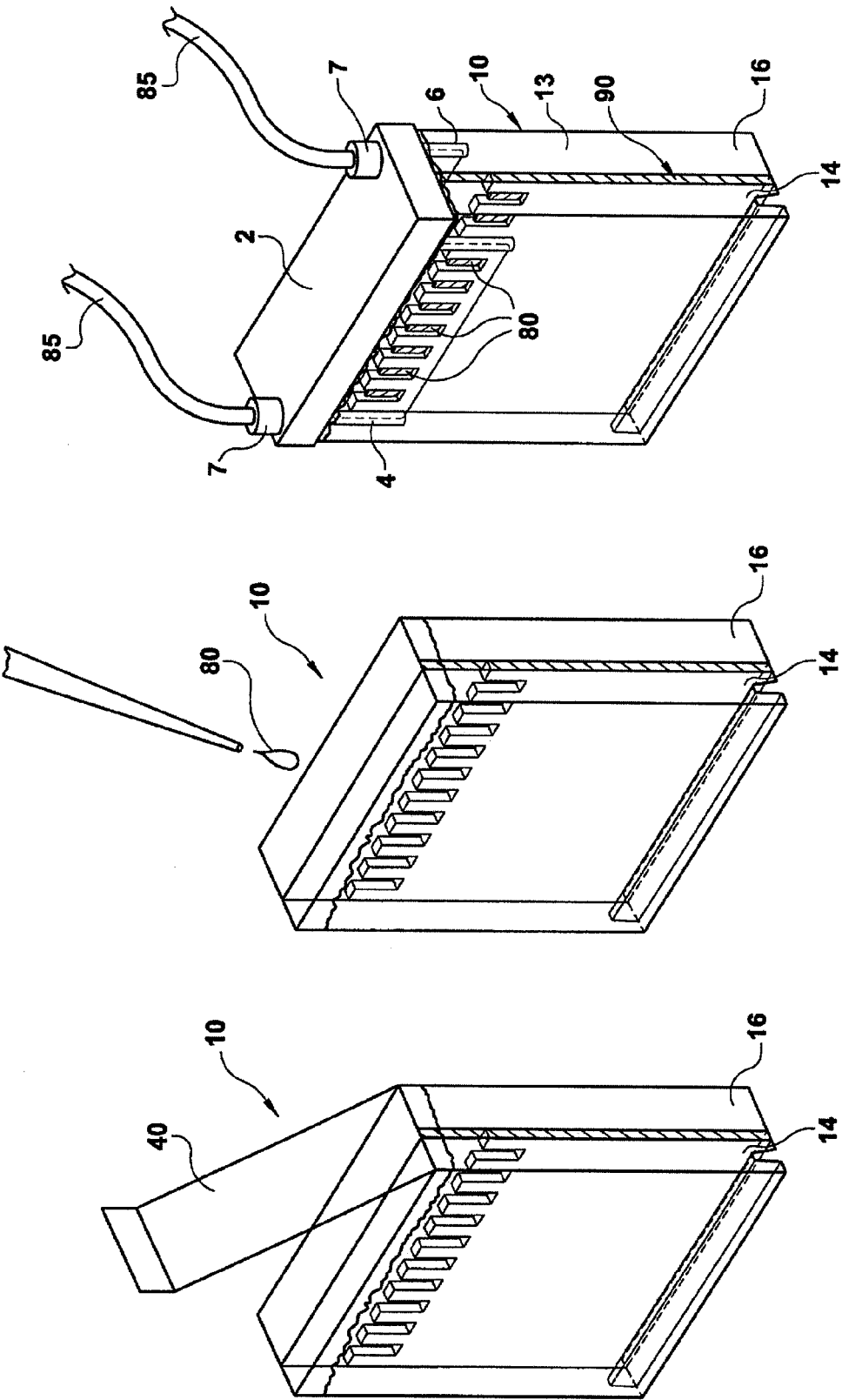
FIG. 7 is a perspective view of one or more embodiments of methods of performing an electrophoresis run using the prefabricated, monolithic gel electrophoresis unit and system of the invention.

As another embodiment of the invention, rather than using a gel comb 45 to provide a plurality of wells 60 in the gel matrix 20, either the first or second interior walls 17, 18 may be provided with a plurality of wells 60 molded directly into an inner surface of such walls 17, 18 as shown in FIGS. 4A and 7. That is, the side of interior wall 17 or 18 that is in direct contact with the gel matrix 20 is fabricated in a manner so that it has a plurality of wells 60 built directly into such wall. These wells 60 reside directly over and in contact with the below separating gel matrix 20 for easily loading the target sample onto or into the gel matrix 20. As another alternative, the walls 17, 18 may each be provided with partial well portions, such that, upon completion of the molded unit 10, entire wells 60 are formed directly over the gel matrix. Additionally, each well 60 built into wall 17 and/or wall 18 may include a marking or color indicator on at least a portion thereof so that the wells are easily distinguished from the rest of unit 10 for loading samples therein.

The top surface of the pre-fabricated, monolithic gel electrophoresis unit 10 is also sealed with a seal 40 prior to performing electrophoresis. This seal 40 is preferably an easily removable layer that prevents leakage of the buffer solution 50 residing inside the unit 10 during transport, handling and storage of such unit prior to the use thereof. For instance, the seal 40 may include, but is not limited to, a easily removable film, tape, glued layer, adhesive layer, and the like. Again, during storage of the monolithic gel electrophoresis unit 10 both seals 40 and 45 tightly seal, respectively, the entire unit 10 and the gel chamber 15 so as to prevent leakage of any buffer from the unit itself and/or prevent contact between the buffer solution 50 and the separating gel matrix 20 (and optionally the stacking gel 22). Further, when the anode chamber 14 contains buffer solution 50, the unit 10 is preferably transported and stored in an inverted position (i.e., upside down) to prevent contact between the buffer solution 50 and base sealing gel 24 residing in the anode chamber 14 since the buffer 50 may degrade the base sealing gel 24.

FIGS. 3A and 4A show the buffer solution 50 residing over seal 45 in the cathode chamber 16 prior to use of the unit 10. As alternative embodiments shown in FIGS. 5A-D, the interior wall 18 that separates the gel chamber 15 from the cathode chamber 16 may extend from the bottom 11 of the unit 10 to the top of the unit 10 and contact the seal 40 prior to use of unit 10. In doing so, an upper portion 18' of the interior wall 18 resides at least above the separating gel matrix 20, preferably above the stacking gel 22, and optionally above seal 45. When the upper portion 18' is in tact and contacting the top seal 40 a cavity 46 resides within the gel chamber 15, which is an empty cavity prior to use of the unit. That is, the upper portion 18' prevents buffer solution 50 from entering such gel chamber prior to use of the unit 10. This is particularly useful for storage and transportation of the unit.

Figure 5D:
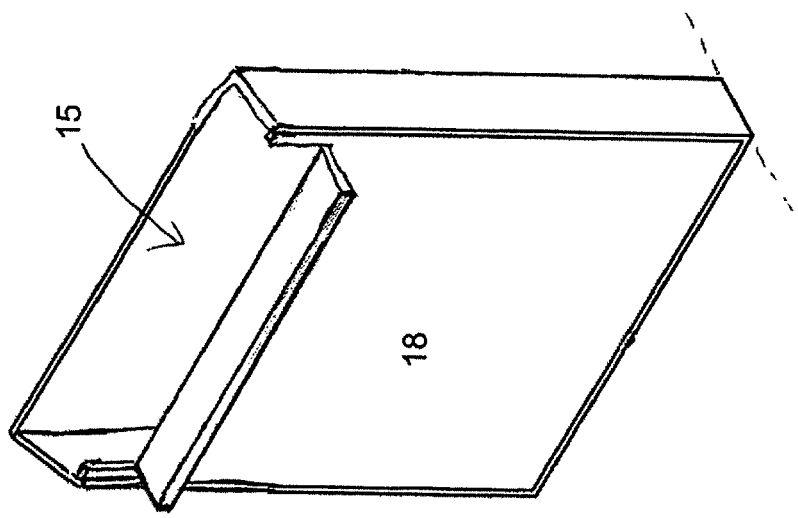
FIGS. 5C-D are perspective views of FIGS. 5A-B.
Figure 5C:
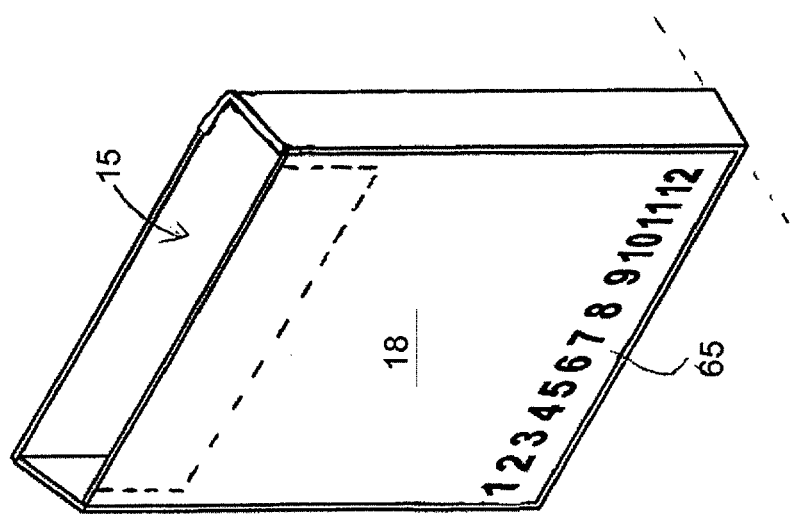

As shown in FIG. 5A, the interior wall that separates the gel chamber from the cathode chamber has a weakened location 118 between the lower portion of the wall 18 and the upper portion 18' of such wall 18. This weakened location 118 allows for easily breaking the wall 18 at such location to allow buffer solution 50 into the gel chamber and at least partially fill the cavity 46 therein. For instance, the weakened location 118 may be a cut-out niche in the wall 18 that allows easy breakage of the wall 18 at such location 118. Once broken, the upper portion 18' may be removed from the unit, or it may be bent down into the cathode chamber and remain there during the electrophoresis run. FIGS. 5C-D show perspective views of only the gel chamber 15 apart from the unit 10 as a whole for ease of viewing and appreciating the upper portion 18' of the interior wall 18 that protects the contents within the gel chamber prior to use of the unit (FIG. 5C) and its breakage to allow buffer solution from the cathode chamber (not shown) into the gel chamber (FIG. 5D).

Figure 6A:
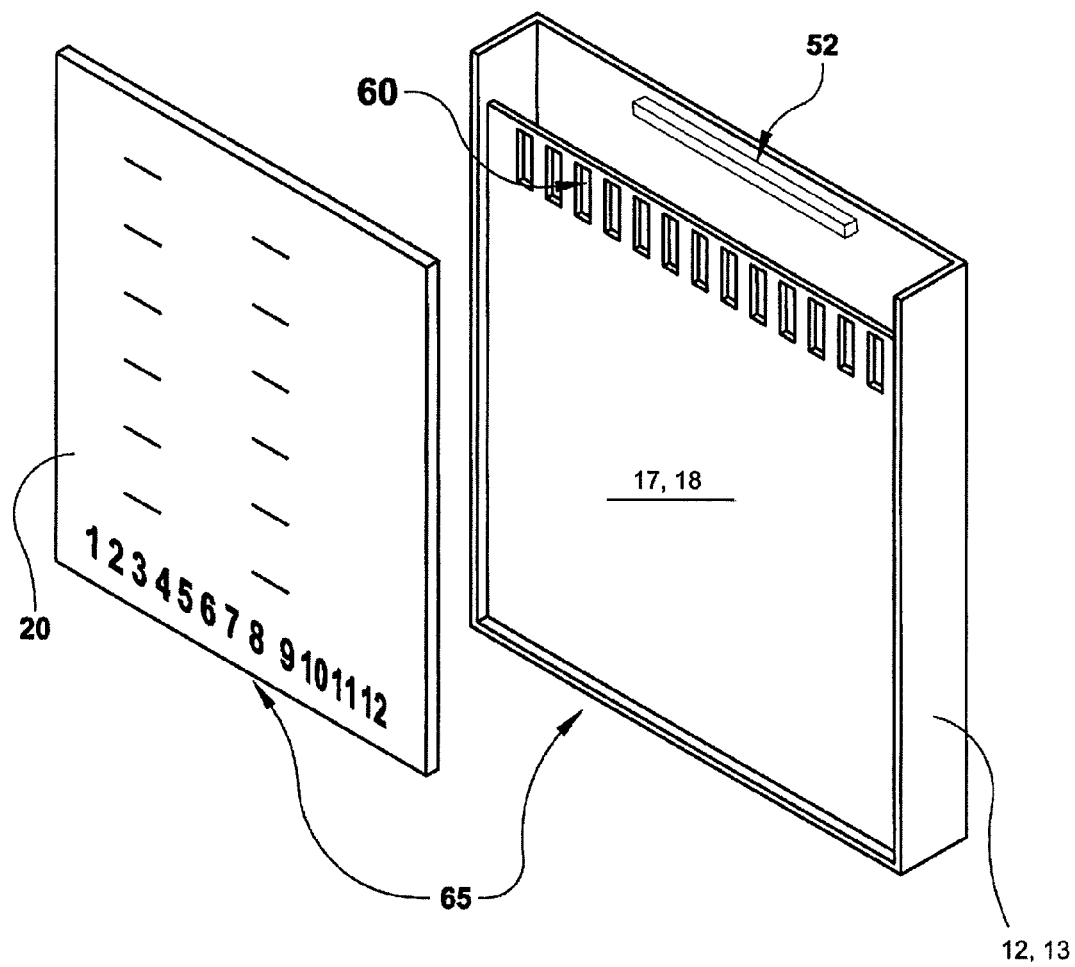

Referring to FIGS. 6A-B, either the separating gel matrix 20 or one of interior walls 17, 18 may further be provided with well indicators 65 comprising, for example, numbers, letters, symbols, etc. Preferably, the well indicators 65 are sequential numbers that reside about 3 mm above the bottom surface of the separating gel matrix 20, wall 17 or wall 18. As such, wall 17 or wall 18 may be provided with one or both of the plurality of wells 60 and/or the well indicators 65. The well indicators 65 preferably correspond to the number of wells 60 (i.e., same number of wells 60 and well indicators 65) for identifying each corresponding well 60. In embodiments where the well indicators 65 reside in or on the separating gel matrix 20, such well indicators may reside directly inside the gel matrix 20 spaced apart to define the individual wells 60 or they may be fabricated on an outside of the gel matrix 20 to identify each well 60. These well indicators 65 may be dyed well indicators fabricated inside or on an outside of the separating gel matrix, separate indicator components (e.g., plastic or glass number pieces) set inside or on an outside of the gel matrix, indicators residing along a strip of material that is set inside or on an outside of the gel matrix, and the like. Alternatively, when the well indicators 65 reside in or on wall 17 or wall 18 these well indicators 65 may be raised above the surface of the wall (i.e., embossed) to form inset (i.e., engraved) well indicators in the separating gel matrix, they may be engraved in the wall to form embossed well indicators in the separating gel matrix, they may be engraved, embossed or planar surface dyed well indicators that are transposed into or onto the separating gel matrix, and the like.

Figure 8:
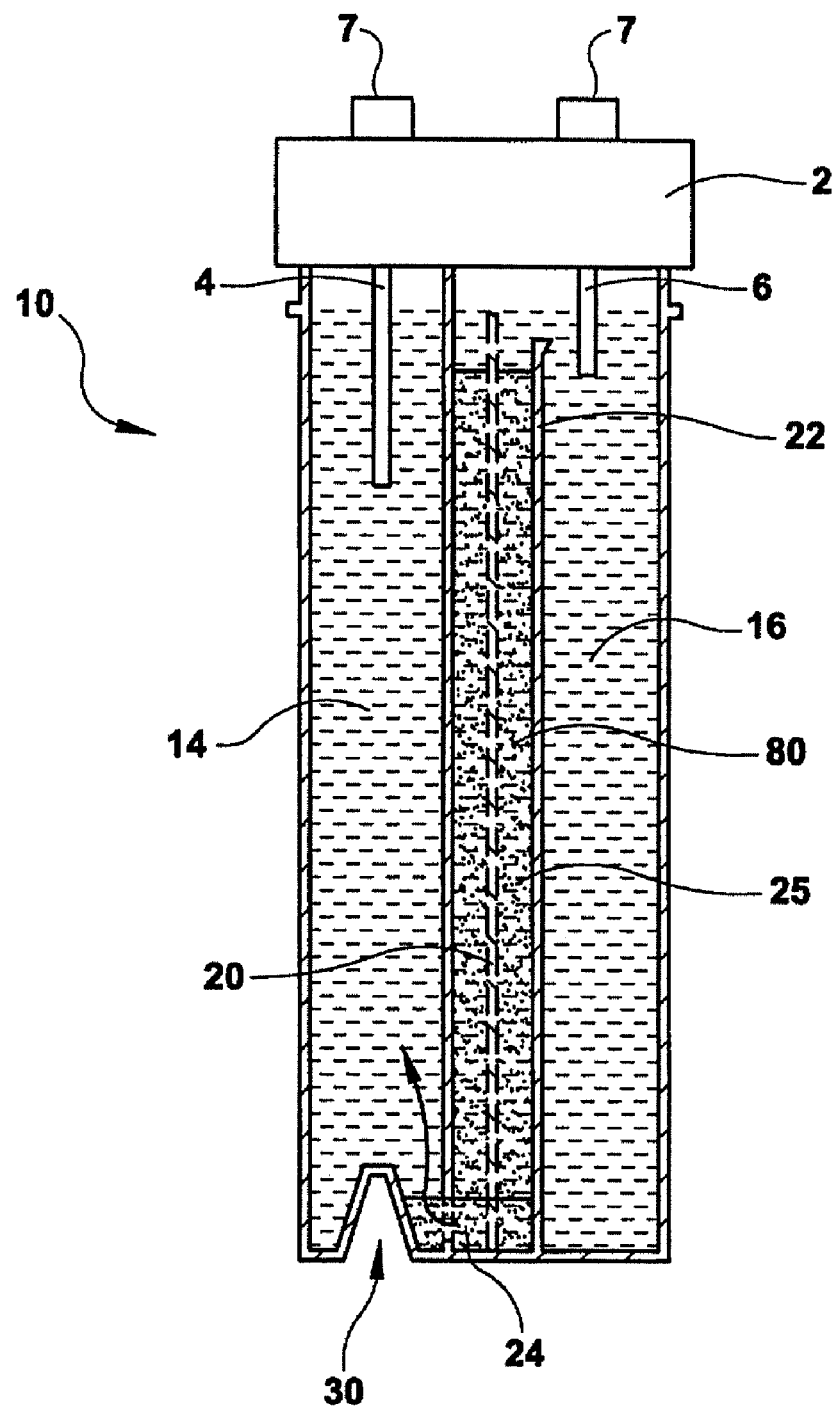
FIG. 8 is a cross-sectional view showing the current flow in one or more embodiments of the monolithic gel electrophoresis system of the invention.
Figure 9:
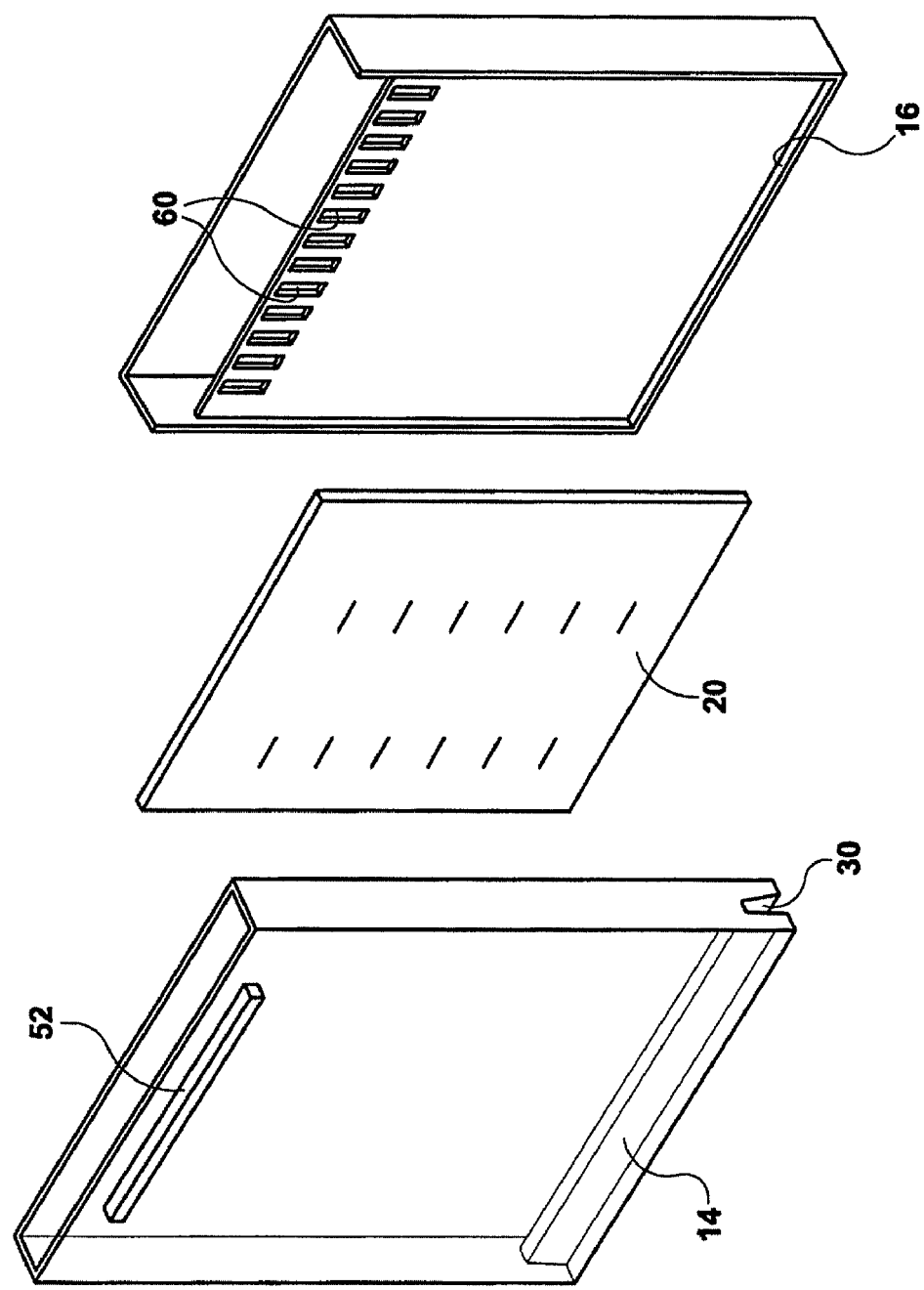
FIG. 9 is a perspective view showing the disassembly of one or more embodiments of the monolithic gel electrophoresis system of the invention.

FIGS. 7-9 shows one embodiment of performing electrophoresis in accordance with the invention using the present pre-fabricated, monolithic gel electrophoresis unit 10. Once a pre-fabricated, monolithic gel electrophoresis unit 10 of the invention has been selected, the unit 10 is provided in its upright position and the seal 40 is removed from the top surface of the unit. For instance, wherein the seal 40 is a layer of removable tape, this tape layer is peeled back and removed from the unit 10. Optionally, the upper portion 18' of wall 18 may be broken at location 118 to allow buffer solution 50 enter into the gel chamber 15. The gel chamber seal 45 that is covering and protecting the gel chamber 15 and the gels therein is also removed from the surface of this gel chamber 15. This may be done either before or after breakage of the wall 18 in those embodiments having the protective upper portion 18' of the wall 18. Again, the gel chamber seal 45 may be a removable layer (e.g., removable tape) or it may be a gel comb 45 that is removed to reveal a plurality of wells 60 residing over the separating gel matrix 20 and between adjacent sections of stacking gel 22.

Once the seals 40, 45 are removed from the unit, buffer solution 50 fills any empty regions inside the gel chamber. In so doing, the pre-loaded buffer solution may fill empty regions of the gel chamber, or if the buffer is in concentrated form, once it is reconstituted, the buffer fills such empty regions inside the gel chamber as shown, for example, in FIG. 3C. Target samples 80 to be tested are then loaded into the wells 60 residing inside the gel chamber(s) 15 of unit 10. Again, these wells 60 may reside in the stacking gel 22, which resides directly over the separating gel 20, or they may reside in interior wall 17 and/or interior wall 18. Regardless, each well 60 is preferably aligned with a corresponding well indicator 65 (which resides inside or outside of either the separating gel 20, interior wall 17 and/or interior wall 18), whereby each well 60 resides directly over the separating gel 20 to reveal top surface portions of the separating gel 20. Since the target samples are generally denser than the buffer solution, these target samples fall to the bottom of the well. It should be appreciated that the volume of the target samples will vary depending upon the well size.

After the target samples 80 are loaded into the wells, the lid 2 is provided over the top surface of unit 10 to form a gel electrophoresis assembly 100 of the invention. Again, the lid 2 is preferably designed so that it can be provided over the unit 10 in only one position so that the anode electrodes 4 are aligned with and provided in the anode chamber 14, while the cathode electrodes 6 are aligned with and provided in the cathode chamber 16. For instance, both the lid 2 and the unit 10 may each have alignment indicators (e.g., color coding, symbols, numbers, letters, etc.) to ensure that the lid 2 is correctly attached to unit 10. The seal 3 of the lid helps to ensure a secure tight fit between the lid 2 and unit 10 once assembled together. The electrodes 4, 6 are electrically connected to corresponding connectors 7 that reside on the outside of the lid 2, which in turn, are connected to a power source (not shown) via power cables 85. These connectors and cables may also be color coded to ensure correct connection to the appropriate positive or negative terminal of the power supply.

An electrical charge is then applied to the gel electrophoresis assembly 100 by turning on the power supply, whereby an effective electrical contact is established between the buffer solution in the cathode chamber 16 and the gel running buffer solution 25 or the buffer solution 50 in the anode chamber 14 through the gel matrices 22 (if present), 20, 24. For instance, referring to FIG. 8, the current flow may flow from the cathode chamber 16 through the gel matrices 22, 20, 24 and into the anode chamber 14. The present electrophoresis assembly 100 is run at an appropriate speed, temperature, power, current, voltage and duration depending upon the gels used and the target samples sufficient to separate the charged molecules into bands within the gel matrix 20.

Once separation has been completed, the power supply is turned off, the lid 2 removed from the monolithic gel electrophoresis unit 10 and any buffer solution 50 within the unit is poured off or out of the unit. Referring to FIGS. 1A, 5 and 7, the monolithic gel electrophoresis unit 10 has a disassembly mechanism 90 on each of the opposing sidewalls 13 for opening the unit 10 by separating the buffer chambers 14, 16 from one another and removing the processed gel matrix 20 for subsequent analytical procedures. This disassembly mechanism 90 preferably extends down the entire length of both sidewalls 13 for easy and efficient opening and disassembly of the unit 10. The disassembly mechanism 90 is preferably designed so that it causes no significant damage to the processed gel matrix 20 upon opening the unit 10. This disassembly region 90 may include, but is not limited to, a sealed groove or channel, a beveled portion, an adhesive seal, ultrasonic welding, a sealant, alumina foil, or any other mechanism for opening the gel electrophoresis unit 10 to remove the gel matrix 20, without damaging such gel matrix 20.

The monolithic gel electrophoresis unit 10 is preferably disposable, whereby after disassembling the unit 10 and removing the gel matrix 20 the chambers 14, 16 are discarded and the lid 2, along with all its components, is retained for subsequent reuse. In this manner, one needs only to select a new monolithic gel electrophoresis unit 10, remove its seals, load target samples, provide the lid 2 over this new unit 10 and perform another electrophoresis run. However, as an alternate embodiment, the chambers 14, 16 may be retained and reused by providing or fabricating a gel using known methods, followed by securing and sealing the gel between the chambers 14, 16 for a subsequent electrophoresis run.

It should be appreciated that the present monolithic gel electrophoresis units 10 may have any desired dimensions as may be desired or required for further downstream processing of the gel matrix. For instance, the pre-fabricated, monolithic gel electrophoresis units 10 may be 9 cm×14 cm×3 cm (i.e., height×length (of outer walls 12)×width (thickness of bottom surface 11)), with a gel matrix 20 having a thickness ranging from <1 mm to about 3 mm, or greater, and requiring less than about 200 ml of buffer solution 50 within the entire unit 10, and even less for those units having buffer solution 50 only in the cathode chamber. While not departing from the novel concepts of the invention, it should be appreciated that the present apparatus and systems may be designed so that the gel matrix is pre-cast horizontally, along with the gel running buffer solution and/or buffer solution chambers and gel chambers residing horizontally, so that the unit 10 is processed in the horizontal position.

The present pre-fabricated, monolithic gel electrophoresis apparatus and systems are compact, all-in-one units that integrate the pre-cast gel matrix and preloaded buffer chambers into single, molded units that are structurally stable and avoid buffer leakage. The compact design of the present pre-fabricated, monolithic gel electrophoresis units 10 provides for easy transportation, storage and use of such units 10. With the pre-cast gel, gel running buffer solution and/or buffer solution all being preloaded into the pre-fabricated, monolithic gel electrophoresis units 10, no other component (other than the lid 2) is need to run the gel. As such, a user merely needs to peel the seals off the unit, (perhaps reconstitute the buffer and/or break and maybe remove the upper portion 18' of the interior wall 18), load target samples into the wells, provide the lid 2 on top of the unit 10, and run the electrophoresis. Accordingly, the one or more embodiments of the invention provide easy and clean to use, low maintenance, easy clean-up (no washing of gel or buffer solution tanks/trays because the entire unit 10 is preferably discarded after use, however, the reusable lid 2 is retained for reuse) and cost effective pre-fabricated, monolithic gel electrophoresis apparatus and systems. There is also reduced upfront costs associated with the present apparatus and systems since one only needs to purchase the reusable lid 2, and not gel or buffer solution tanks/trays, clamps, gel holders, etc.

Figure 10:
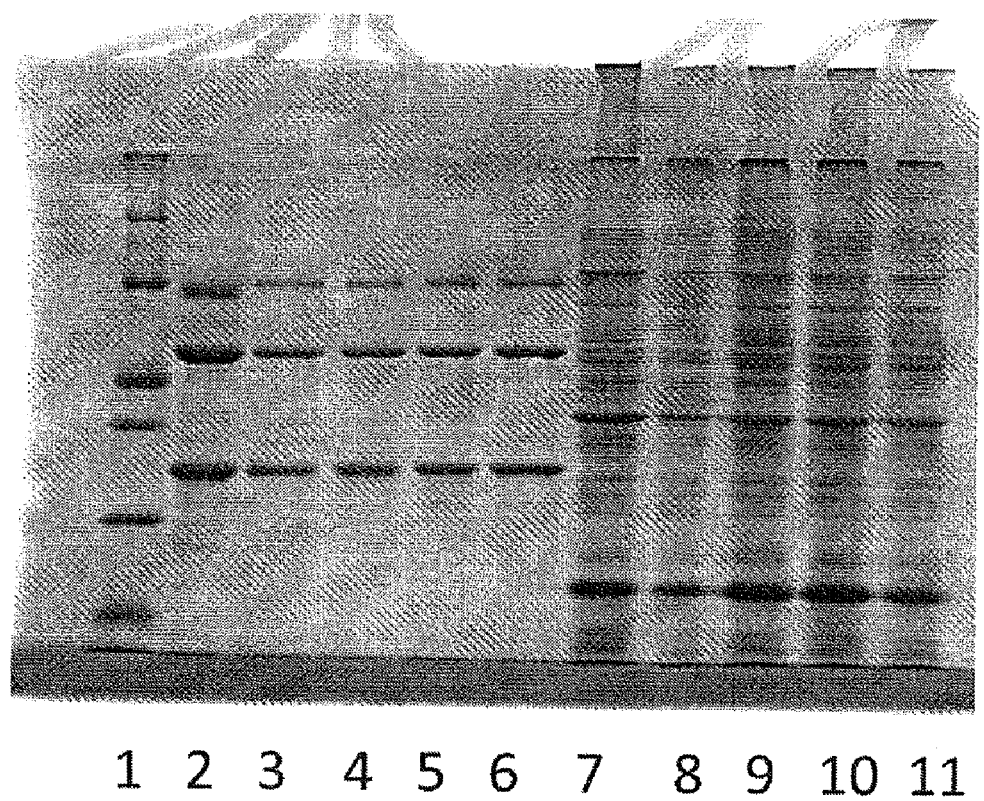
FIG. 10 shows the gel matrix results after performing electrophoresis using a prefabricated, monolithic gel electrophoresis unit and system of the invention.

Experimental Results: FIG. 10 shows the results of performing electrophoresis on a gel matrix 20 within a unit 10 of the invention. These results were obtained by running an electrophoresis unit 10 having a gel matrix 20 between anode and cathode chambers, whereby the anode chamber contained a gel running buffer solution of the same composition as the gel matrix 20 while the cathode chamber contained a buffer solution. The gel comprised 12% gel constituted with 200 mM citrate-HCL, pH 6.9 as the gel running buffer solution. The anode chamber contained a gel running buffer of 200 mM citrate-HCL, pH 6.9, and the cathode chamber contained a buffer solution of 100 mM Tri-Hepes, pH 7.8. Lane 1 in FIG. 10 shows the protein molecular weight markers, Lanes 2-6 show three protein mixtures, and Lanes 7-11 *E. Coli* whole cells. As can be seen in FIG. 10, proteins are well resolved in the gel. The bands are very sharp. It has been found that the results shown in FIG. 10 are substantially comparable with gel matrix results after performing electrophoresis using a prefabricated, monolithic gel electrophoresis unit and system of the invention whereby the gel matrix was run with 100 mM Tri-Hepes, pH 7.8, buffer in both that anode and cathode chambers.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A one-piece electrophoresis apparatus for use in performing gel electrophoresis comprising:
   a separating gel matrix comprising a gel and a gel running buffer solution;
   at least one gel chamber containing a pre-cast gel comprising at least said separating gel matrix,
   a first chamber containing said gel running buffer solution;
   a second chamber containing a buffer solution;

said gel chamber and said first and second chambers are integrated with each other into a single unit that comprises a molded monolithic electrophoresis unit ready for use; and a unit seal of said single unit residing on and completely covering and sealing top surfaces of the first buffer chamber, the second buffer chamber and the gel chamber containing the pre-cast gel prior to use of said single unit.

2. The apparatus of claim 1 wherein said first chamber comprises an anode chamber and said second chamber comprises a cathode chamber, said at least one gel chamber residing in electrical communication with both said cathode chamber and said anode chamber.

3. The apparatus of claim 2 wherein said gel chamber is in contact with said cathode chamber and separated from said anode chamber by a sealing gel, said sealing gel filling an opening of said single unit and residing between and within said gel chamber and said anode chamber.

4. The apparatus of claim 2 wherein said single unit further includes a third chamber comprising another anode chamber containing said gel running buffer and a plurality of gel chambers each containing individual pre-cast gels, whereby each of said plurality of gel chambers is separated from said anode chambers by a sealing gel.

5. The apparatus of claim 1 wherein said pre-cast gel comprises in sequence a sealing gel, said separating gel matrix and a stacking gel.

6. The apparatus of claim 1 wherein said single unit further includes a volume marker that indicates a fill line of said buffer and said gel running buffer.

7. The apparatus of claim 6 wherein said buffer and said gel running buffer solutions comprise preloaded solutions filled to said fill line.

8. The apparatus of claim 6 wherein said buffer solution comprises a concentrated buffer composition that requires reconstitution to said fill line prior to use of said single unit.

9. The apparatus of claim 1 further including inside said single unit a plurality of molded wells in contact with said pre-cast gel.

10. The apparatus of claim 1 wherein said unit seal comprises a removable layer selected from the group consisting of a removable film, tape, glued layer and adhesive layer.

11. The apparatus of claim 1 wherein said molded monolithic electrophoresis unit comprises a vertical molded monolithic electrophoresis unit.

12. The apparatus of claim 1 further including a gel chamber seal residing on a top surface of said gel chamber, thereby preventing contact between said pre-cast gel and said buffer solution prior to use of said single unit.

13. The apparatus of claim 12 wherein said gel chamber seal comprises a removable comb having a plurality of teeth extending into said pre-cast gel, thereby forming a plurality of wells in said pre-cast gel.

14. The apparatus of claim 12 wherein said gel chamber seal comprises a removable layer selected from the group consisting of a removable film, tape, glued layer and adhesive layer.

15. The apparatus of claim 1 further including a sealing wall residing between said gel chamber and said cathode chamber to prevent contact between said pre-cast gel and said buffer solution prior to use of said single unit.

16. The apparatus of claim 15 wherein said sealing wall is at least breakable to allow said buffer solution enter into said gel chamber.

17. The apparatus of claim 1 further including well indicators residing inside said single unit to identify a plurality of wells of said pre-cast separating gel matrix.

18. The apparatus of claim 1 further including a disassembly mechanism on at least a pair of exterior walls of said single unit that enable opening of said single unit after use thereof.

19. A system for use in performing gel electrophoresis comprising:
a reusable lid;
a pre-fabricated monolithic electrophoresis unit comprising:
a separating gel matrix comprising a gel and a gel running buffer solution;
an anode chamber containing said gel running buffer solution,
a cathode chamber containing a buffer solution,
a gel chamber integrated with and residing between said anode and cathode chambers and containing a pre-cast gel comprising at least said separating gel matrix,
a unit seal residing on and completely covering and sealing top surfaces of the anode buffer chamber, the cathode buffer chamber and the gel chamber containing the pre-cast gel prior to use of the pre-fabricated unit, said pre-fabricated monolithic electrophoresis unit being ready for use in performing gel electrophoresis; and
an electrical connection between said reusable lid and said pre-fabricated monolithic electrophoresis unit to perform said gel electrophoresis.

20. A method for performing gel electrophoresis comprising:
providing a monolithic electrophoresis unit having a unit seal on a top surface thereof comprising:
an anode chamber containing a gel running buffer solution,
a cathode chamber containing a buffer solution,
a gel chamber having a gel chamber seal integrated with and residing between said anode and cathode buffer chambers and containing a pre-cast gel comprising at least a separating gel matrix including a gel and said gel running buffer solution,
a unit seal residing on and completely covering top surfaces of the anode buffer chamber, the cathode buffer chamber and the gel chamber prior to use of the monolithic electrophoresis unit;
removing said unit seal and said gel chamber seal;
loading a target sample into said monolithic electrophoresis unit;
attaching a reusable lid to said top surface of said monolithic electrophoresis unit; and
performing electrophoresis to said pre-cast gel by providing an electrical connection through said reusable lid into said monolithic electrophoresis unit.

* * * * *

UNITED STATES PATENT AND TRADEMARK OFFICE
CERTIFICATE OF CORRECTION

PATENT NO. : 8,361,294 B2  
APPLICATION NO. : 12/792953  
DATED : January 29, 2013  
INVENTOR(S) : Yi Wang Page 1 of 1

It is certified that error appears in the above-identified patent and that said Letters Patent is hereby corrected as shown below:

In the Specification

Column 4, Line 51, delete "Figs. 1A-1B" and substitute therefor -- Figs. 1A-1C --.

Column 4, Line 63, after "additional" insert therefor -- running solution (e.g., buffer or gel running --.

Column 4, Line 63, delete "buffer" and substitute therefor -- buffer) --.

Signed and Sealed this  
Twenty-sixth Day of November, 2013

Margaret A. Focarino  
*Commissioner for Patents of the United States Patent and Trademark Office*